(12) United States Patent
Yu et al.

(10) Patent No.: US 10,881,677 B2
(45) Date of Patent: Jan. 5, 2021

(54) COMPOSITION FOR MODULATING IRAK1

(71) Applicant: Agency for Science, Technology and Research, Singapore (SG)

(72) Inventors: Qiang Yu, Singapore (SG); Zhen Ning Wee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/770,437

(22) PCT Filed: Oct. 24, 2016

(86) PCT No.: PCT/SG2016/050518
§ 371 (c)(1),
(2) Date: Apr. 23, 2018

(87) PCT Pub. No.: WO2017/069710
PCT Pub. Date: Apr. 27, 2017

(65) Prior Publication Data
US 2018/0311264 A1 Nov. 1, 2018

(30) Foreign Application Priority Data
Oct. 23, 2015 (SG) ............. 10201508795X

(51) Int. Cl.
*A61K 31/704* (2006.01)
*C12Q 1/6886* (2018.01)
*A61P 35/00* (2006.01)
*G01N 33/574* (2006.01)

(52) U.S. Cl.
CPC ............ *A61K 31/704* (2013.01); *A61P 35/00* (2018.01); *C12Q 1/6886* (2013.01); *C12Q 2600/106* (2013.01); *C12Q 2600/118* (2013.01); *C12Q 2600/158* (2013.01); *G01N 33/57415* (2013.01); *G01N 2333/5412* (2013.01); *G01N 2333/5421* (2013.01); *G01N 2800/52* (2013.01)

(58) Field of Classification Search
CPC ......... A61K 6/00; A61K 31/00; A61K 31/70; A61K 31/7028; A61K 31/7034; A61K 31/704; A61P 1/00; A61P 35/00; C12Q 1/00; C12Q 1/68; C12Q 1/6876; C12Q 1/6883; C12Q 1/6886; C12Q 2600/00; C12Q 2600/106; C12Q 2600/118; C12Q 2600/158; G01N 1/00; G01N 33/574; G01N 33/57407; G01N 33/57415; G01N 2800/00; G01N 2800/52
See application file for complete search history.

(56) References Cited

U.S. PATENT DOCUMENTS

2006/0160114 A1* 7/2006 Kerfoot ............... C12Q 1/6886
435/6.16
2013/0280264 A1* 10/2013 Davila ................ C12Q 1/6886
424/142.1
2014/0018361 A1 1/2014 Harriman et al.

FOREIGN PATENT DOCUMENTS

| WO | WO 01/82908 A2 | 11/2001 |
| WO | WO 2012/097013 A1 | 7/2012 |
| WO | WO 2013/106535 A1 | 7/2013 |
| WO | WO 2015/048281 A1 | 4/2015 |
| WO | WO 2015/164374 A1 | 10/2015 |

OTHER PUBLICATIONS

Qiao Li, 人参皂苷 Rg3 联合卡培他滨治疗晚期 三阴性乳腺癌的 临床疗效研究 —Hebei Medical Journal. Aug. 30, 2015; 37(16):2445-7. DOI: 10.3969/J.ISSN.1002-7386.2015.16.013.
PCT/SG2016/050518, Jan. 26, 2017, International Search Report and Written Opinion.
International Search Report and Written Opinion dated Jan. 26, 2017 in connection with International Application No. PCT/SG2016/050518.
Jia et al., Rh2, a compound extracted from ginseng, hypersensitizes multidrug-resistant tumor cells to chemotherapy. Can J Physiol Pharmacol. Jul. 2004;82(7):431-7.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Liu et al., FOXP3 Controls an miR-146/NF-κB Negative Feedback Loop That Inhibits Apoptosis in Breast Cancer Cells. Cancer Res. Apr. 15, 2015;75(8):1703-13. doi: 10.1158/0008-5472.CAN-14/2108. Epub Feb. 23, 2015.
Pinto et al., A score based in Toll-Like Receptors expression to predict prognostic in molecular subtypes of breast cancer treated with neoadjuvant chemotherapy (NAC). J Clin Oncol. Jun. 4, 2013; 31:e22165. Abstract only.
Scheeren et al., A cell-intrinsic role for TLR2-MYD88 in intestinal and breast epithelia and oncogenesis. Nat Cell Biol. Dec. 2014;16(12):1238-48. doi: 10.1038/ncb3058. Epub Nov. 2, 2014.

(Continued)

*Primary Examiner* — Alana Harris Dent
(74) *Attorney, Agent, or Firm* — Wolf, Greenfield & Sacks, P.C.

(57) ABSTRACT

The present invention relates to the treatment of breast cancer, more particularly triple negative breast cancer (TNBC), with the use of an inhibitor of Interleukin 1 Receptor Associated Kinase 1 (IRAK1) such as ginsenosides. It also relates to a method for aiding in categorising or determining prognosis in a breast cancer patient or in selecting a therapeutic strategy comprising assessing the level of IRAK1 nucleic acid, protein or activity in a sample and, in some aspects, further assessing the paclitaxel resistance status of the patient and if the patient is resistant to paclitaxel therapy, treating the patient with an inhibitor of IRAK1 activity. In addition, a screening method for identifying a compound useful for treating breast cancer comprises determining the effect of a test compound on IRAK1 nucleic acid, protein or activity level and selecting a compound that reduces said level.

Figure 1:
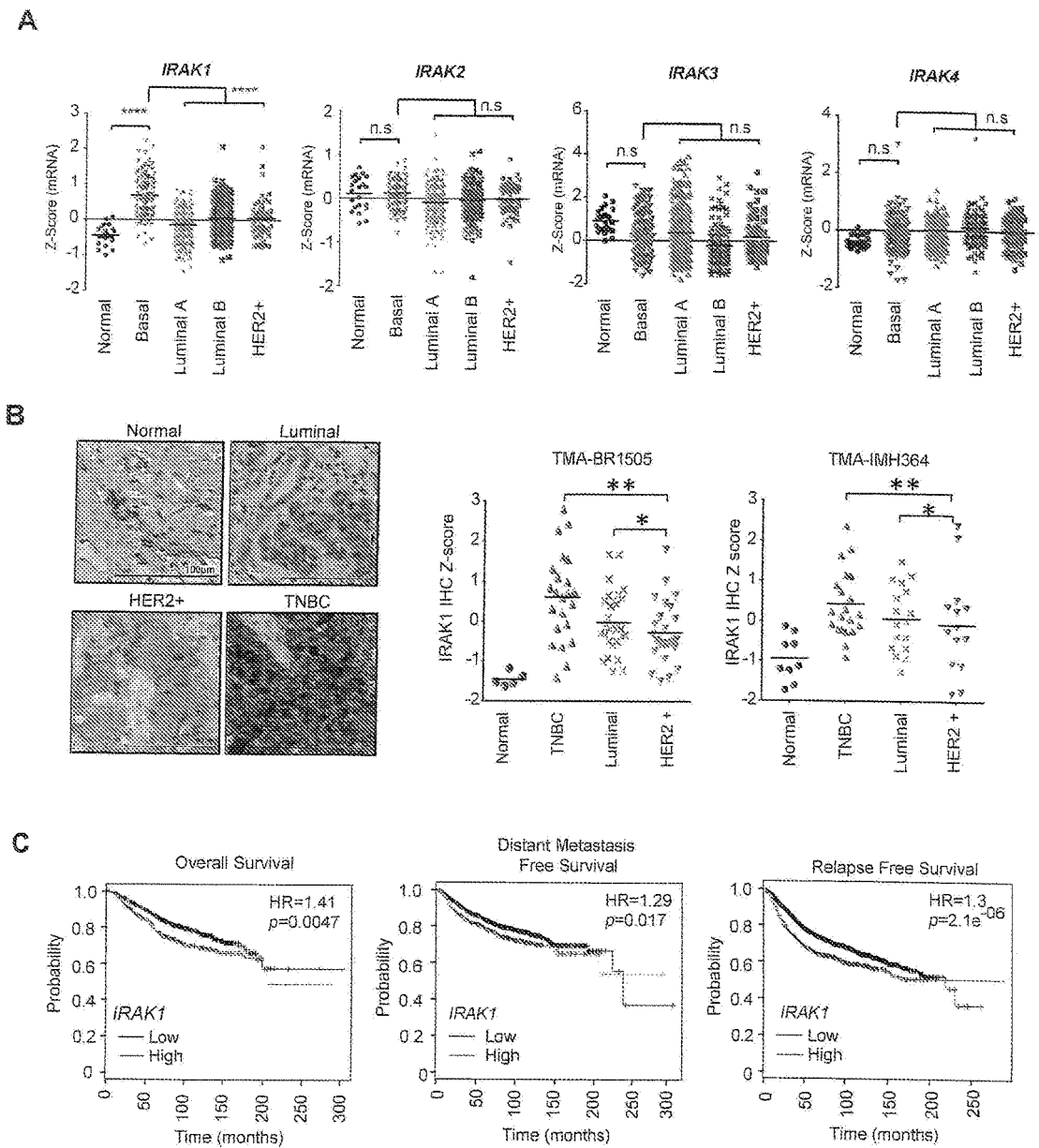

2 Claims, 19 Drawing Sheets
Specification includes a Sequence Listing.

(56) References Cited

OTHER PUBLICATIONS

Wee et al., IRAK1 is a therapeutic target that drives breast cancer metastasis and resistance to paclitaxel. Nat Commun. Oct. 27, 2015;6:8746. doi: 10.1038/ncomms9746.

Yang et al., Enhanced oral bioavailability and anti-tumour effect of paclitaxel by 20(s)-ginsenoside Rg3 in vivo. Biopharm Drug Dispos. Nov. 2012;33(8):425-36. doi: 10.1002/bdd.1806. Epub Sep. 21, 2012.

* cited by examiner (a)

(b)

(a)

(b)

(a)

(b)

| Drug | Parental MDA231 (IC$_{50}$, M) | Paclitaxel-treated MDA231 (IC$_{50}$, M) | Fold change (paclitaxel-treated vs parental) |
|---|---|---|---|
| Paclitaxel | 4.62e-09 | 2.65e-07 | 57.38 |
| Doxorubicin | 1.97e-07 | 0.000001 | 6.55 |
| Vincristine | 9.32e-10 | 4.38e-09 | 4.70 |
| 5-FU | 0.00004 | 0.00007 | 1.64 |
| Cisplatin | 5.40e-05 | 5.76e-05 | 1.07 |
| Gemcitabine | 3.30e-07 | 2.93e-07 | 0.89 |
| Pacritinib | 0.000003 | 8.85e-07 | 0.31 |

Figure 17 (c)

COMPOSITION FOR MODULATING IRAK1

CROSS-REFERENCE TO RELATED APPLICATIONS

This application is the National Phase filing under 35 U.S.C. § 371 of PCT International Patent Application Serial No. PCT/SG2016/050518, filed Oct. 24, 2016, which claims the benefit and priority to Singapore application no. 10201508795X, filed 23 Oct., 2015 the entire contents of the aforementioned applications are hereby incorporated herein by reference.

The present invention relates to assessment and treatment of cancer. In particular, the present invention relates to the assessment and treatment of breast cancer, more particularly triple negative breast cancer.

Management of triple negative breast cancers, TNBC. These cancers are particularly aggressive and have a propensity for early recurrence and death.

TNBC is a unique subtype of breast cancer defined by the absence of estrogen receptor (ER), progesterone receptor (PR) and human epidermal growth factor receptor type 2 (HER2)[1]. It accounts for approximately 15-20% of all breast cancers[2] and 85% of all basal-like breast cancer[3]. Unlike other subtypes of breast cancers, TNBC is frequently associated with an overall poor prognosis characterized by a higher rate of recurrence and distant metastasis and has no effective targeted therapies.

Chemotherapy is the only systemic modality available for the treatment of TNBC and it is perhaps fortunate that TNBC have a higher pathological response compared to ER-positive tumours. Despite this, disease recurrence is high and often occurs within the first 3 years. Although chemotherapy is effective initially in a subset of patients, the disease often recurs and progresses aggressively due to acquired chemoresistance, resulting in a shorter overall survival as compared to other subtypes of breast cancer[4]. The outcome is worse in those who fail to achieve complete pathological response (pCR). Despite being a major cause of mortality, treatment options for advanced TNBC remains limited, necessitating identification of new therapeutic strategies that target chemoresistance and metastasis. Current guidelines do not recommend further chemotherapy for residual disease after neoadjuvant chemotherapy and seems contrary to the poor prognosis, which we have similarly observed in our patients. The reason for this apparent under-treatment arises primarily because of the uncertainty of the clinical benefit to justify the additional toxicity.

The current biomarkers ER and PR predict chemotherapy response to a very limited extent and allude to the molecular diversity among breast tumours. Even among TNBC, chemotherapy response varies; basal-like BL-subtypes having the highest pCR rates. Multigene panel assays, such as Oncotype DX, were developed to stratify chemotherapy benefit according to selected gene expression patterns. Apart from being limited to ER-positive tumours, these assays, as in the case of Oncotype DX, fail to give a definite recommendation in the 40% of patients with an indeterminate score (SABCS 2015). Molecular diversity also results in differential response to the same chemotherapeutic agent. While chemo-predictive biomarkers have been reported, most are not sufficiently validated for clinical use and predict resistance to a single agent alone, offering clinicians little practical advice on a suitable alternate non-cross resistant agent. Thus what is needed is a biomarker that not only predicts which tumours are expected to benefit from chemotherapy, but also the agents the tumour is likely sensitive to.

Another challenge in TNBC is the lack of therapeutic targets. The prognosis of HER2-overexpressing tumours improved dramatically with the addition of trastuzumab. Much work is thus focused on developing targeted therapeutics. Poly (ADP-ribose) polymerase (PAPR) inhibitors are being explored based on preclinical data of efficacy in TNBC with deficient homologous recombination repair, even in the absence of BRCA1/2 mutations. PI3K, MEK and mTOR inhibitors are being explored in specific subgroups and recently, the Jak2 inhibitor showed promise in TNBC with JAK2 amplification. It is likely that any of these targeted therapeutics will be effective in only a fraction of TNBC given the diversity and specificity of such agents; for comparison, trastuzumab is effective in only 25% of breast cancers.

Inflammatory response plays a crucial role in cancer progression[5-7]. In particular, inflammatory cytokine and chemokine production, elicited by pathways such as NF-κB, Jak/Stats, and IFNs, has been linked to cancer initiation, metastasis and chemoresistance[8-10]. In breast cancer, constitutive activation of NF-κB has been found to be more frequent in TNBC, which can be elicited by both autocrine and paracrine mechanisms, leading to expression of a myriad of downstream targets including inflammatory cytokines, such as IL-6, IL-8 and CXCLs and anti-apoptotic genes to confer aggressive growth, stemness and chemoresistance[11-14]. Although NF-κB appears to be an excellent target for cancer therapy, development of NF-κB inhibitors have not been able to provide clinical benefits as they cause severe toxicity to the normal tissues due to an essential function of NF-κB in normal cells as well[15-18]. As such, effort has been invested to develop therapeutic strategies that selectively target cancer-specific NF-κB downstream events in order to spare the normal cells[19]. Alternatively, we reasoned that identification of an actionable oncogenic upstream event that confers NF-κB dependency in cancer cells but not normal cells may also warrant therapeutic exploration in the treatment of NF-κB-driven human cancers like TNBC.

Toll-like receptors (TLRs)/Interleukin 1-receptor (IL-1R) signaling engages IRAK4 and IRAK1 phosphorylation to drive downstream events such as NF-κB and interferon signaling in inflammation response and this process has been recently implicated in tumorigenesis[20-23]. Moreover, pharmacologic inhibition of IRAK1/4 has been shown to be efficacious in targeting MDS and acute lymphoblastic leukemia (ALL) that carry IRAK1 activation through NF-κB-dependent or in-dependent mechanism[20,22].

The listing or discussion of an apparently prior-published document in this specification should not necessarily be taken as an acknowledgement that the document is part of the state of the art or is common general knowledge.

Any document referred to herein is hereby incorporated by reference in its entirety.

In the present invention, we elucidated an oncogenic role of interleukin 1 receptor associated kinase 1 (IRAK1) in a subset of TNBC, and demonstrated its functional connection to metastasis and chemoresistance through both NF-κB-dependent and independent mechanisms. Activation of IRAK1 signaling was observed in TNBC cells that acquired resistance to paclitaxel and consequently, inhibition of the pathway induced massive apoptosis. This activation of IRAK1 signaling appeared to be specific to paclitaxel and p-IRAK1-overexpressing cells remained sensitive to cisplatin and gemcitabine. We therefore hypothesise that p-IRAK1 can identify paclitaxel-resistant TNBC that may benefit from further treatment with the alternate non-cross resistant agents cisplatin and gemcatibine. Importantly, we show that pharmacologic inhibitors of IRAK1, including a nature product, are robustly active against TNBC metastasis and chemoresistance, thus providing a readily explorable therapeutic strategy for targeting refractory TNBC which is currently incurable.

In addition, it follows also that IRAK1 may have the potential as a therapeutic target in itself. MDA-MB-231 cells expressing high levels of p-IRAK1 were no longer susceptible to increasing doses of paclitaxel, but massive apoptosis was observed when the IRAK1 inhibitor, IRAK-inh, was added to inhibit IRAK1 signaling. The JAK2 inhibitor, pacritinib, was also found to have IRAK1-inhibitory activity (through communication with CTI BioPharma) and treatment of paclitaxel-resistant MDA-MB-231 cells with pacritinib produced effects similar to those seen with IRAK-inh. We therefore hypothesise that IRAK1 may be a novel therapeutic target in TNBC tumours with acquired resistance to first-line agent paclitaxel. In fact, IRAK1 inhibition has also been explored as a therapeutic modality in myelodysplastic syndrome and acute myeloid leukaemia.

Hence, in a first aspect of the present invention, there is provided the use of a composition that modulates IRAK1 in the manufacture of a medicament for treating cancer, for example breast cancer, ovarian cancer, lung cancer or pancreatic cancer among others.

Preferably, the term modulates refers to an activation, inhibition, delay, repression or interference of one or more of: the activity of IRAK1; the phosphorylation of IRAK1; or the level of expression of IRAK1 including both mRNA expression and protein expression. More preferably, the term modulates refers to a reduction in the levels of IRAK1.

Preferably, the breast cancer is triple negative breast cancer.

Preferably, the composition comprises a ginsenoside. Ginsenosides belong to a class of natural product steroid glycosides and triterpene saponins. Compounds in this family are found almost exclusively in the plant genus *Panax* (*ginseng*), which has a long history of use in traditional medicine that has led to the study of pharmacological effects of *ginseng* compounds. As a class, ginsenosides exhibit a large variety of subtle biological effects when studied in isolation. Ginsenosides can be isolated from various parts of the plant, though typically from the roots, and can be purified by column chromatography. The chemical profiles of *Panax* species are distinct; although Asian *ginseng*, *Panax ginseng*, has been most widely studied due to its use in traditional Chinese medicine, there are ginsenosides unique to American *ginseng* (*Panax quinquefolius*) and Japanese *ginseng* (*Panax japonicus*). Ginsenoside content also varies significantly due to environmental effects.

In one embodiment, the composition may be a pharmaceutical composition that includes a pharmaceutically acceptable carrier. Preferably, the composition is a unit dosage containing a daily dose or unit, daily sub-dose or an appropriate fraction thereof, of the active ingredient. In human therapy, the compositions can be administered alone but will generally be administered in admixture with a suitable pharmaceutical excipient diluent or carrier selected with regard to the intended route of administration and standard pharmaceutical practice.

Preferably, the composition is suitable for parenteral administration to a patient. Compositions suitable for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In another aspect of the present invention, there is provided an inhibitor of IRAK1 activity for use in treating a breast cancer patient. In an embodiment, the patient is administered a further anti-cancer agent or treatment.

In another aspect of the present invention, there is provided a method for aiding in categorising or determining prognosis in a patient with breast cancer, or in selecting a therapeutic strategy for a patient with breast cancer, the method comprising assessing the level of IRAK1 nucleic acid, protein or activity in a sample. Determination of the level of IRAK1 and phosphorylated IRAK1 in the sample will be useful to the clinician in determining how to diagnose and/or manage the cancer and decide the chemotherapy strategy in the patient. In addition, determination the level of IRAK1 will also be useful in determining the probably of a relapse in a patient.

In an embodiment, the breast cancer is triple negative breast cancer.

In addition, the method comprising the step of assessing the level of NF-κB nucleic acid, protein or activity in the sample.

In addition, or alternatively, the method may further comprise the step of assessing the level of IL-6, IL-8 or CSCL1 nucleic acid, protein or activity in the sample.

Advantageously, the method includes the step of selecting a treatment regime making use of the information on the level of IRAK1 nucleic acid, protein or activity in the sample.

Preferably, the sample is a tissue sample in which breast cancer is suspected or in which breast cancer has been found, or contains cells from said tissue.

It is preferred if the nucleic acid is derived from a sample of the tissue in which cancer is suspected or in which cancer may be or has been found. For example, if the tissue in which cancer is suspected or in which cancer may be or has been found is breast, it is preferred if the sample containing nucleic acid is derived from the breast (including armpit tissue, for example lymph node tissue) of the patient. Samples of breast may be obtained by surgical excision, "true cut" biopsies, needle biopsy, nipple aspirate, aspiration of a lump or image-guided biopsy. The image may be generated by X-ray, ultrasound or (less preferably) technetium-99-labelled antibodies or antibody fragments which bind or locate selectively at the breast. Magnetic resonance imaging (MRI) may be used to distinguish fibrosis from breast cancer. The sample may also be biopsy or needle aspirate of a suspected metastatic site such as the liver or lungs or bones.

The sample may be directly derived from the patient, for example, by biopsy of the tissue, or it may be derived from the patient from a site remote from the tissue, for example because cells from the tissue have migrated from the tissue to other parts of the body. Alternatively, the sample may be indirectly derived from the patient in the sense that, for example, the tissue or cells therefrom may be cultivated in vitro, or cultivated in a xenograft model; or the nucleic acid sample may be one which has been replicated (whether in vitro or in vivo) from nucleic acid from the original source from the patient. Thus, although the nucleic acid derived from the patient may have been physically within the patient, it may alternatively have been copied from nucleic acid which was physically within the patient. The tumour tissue may be taken from the primary tumour or from metastases. The sample may be lymph nodes, lymph or blood and the spread of disease detected. It will be appreciated that the aforementioned methods may be used for presymptomatic screening of a patient who is in a risk group for cancer. High risk patients for screening include patients over 50 years of age or patients who carry a gene resulting in increased susceptibility (e.g. predisposing versions of BRCA1, BRCA2 or p53); patients with a family history of breast/ovarian cancer; patients with affected siblings; nulliparous women; and women who have a long interval between menarche and menopause. Similarly, the methods may be used for the pathological classification of tumours such as breast tumours.

Quantitative analysis by immunohistochemically processed tissue sections may be used. It may be useful to assess separately nuclear and cytoplasmic IRAK1 protein, for example as described below, but the skilled person would be able to carry out any suitable process to assess protein quantity, for example an antibody that is considered to react with IRAK1 may be used. The level of IRAK1 protein may be, for example, at least visualised as being much higher in cancerous cells with a high probability of relapse than in cancerous cells with a low probability of relapse or in non-cancerous cells as measured by immunohistochemistry.

It is preferred that if the sample containing nucleic acid (eg mRNA) derived from the patient is not a substantially pure sample of the tissue or cell type in question that the sample is enriched for the said tissue or cells. For example, enrichment for breast cells in a sample such as a blood sample may be achieved using, for example, cell sorting methods such as fluorescent activated cell sorting (FACS) using a breast cell-selective antibody, or at least an antibody which is selective for an epithelial cell. The source of the said sample also includes biopsy material as discussed above and tumour samples, also including fixed paraffin mounted specimens as well as fresh or frozen tissue. The nucleic acid sample from the patient may be processed prior to contact with the nucleic acid which selectively hybridises to the IRAk1 mRNA. For example, the nucleic acid sample from the patient may be treated by selective amplification, reverse transcription, immobilisation (such as sequence specific immobilisation), or incorporation of a detectable marker.

Cells may be analysed individually, for example using single-cell immobilisation techniques. Methods by which single cells may be analysed include methods in which the technique of Laser Capture Microdissection (LCM) is used. This technique may be used to collect single cells or homogeneous cell populations for molecular analysis and is described in, for example, Jin et al (1999) Lab Invest 79(4), 51 1-512; Simone et al (1998) Trends Genet 14(7), 272-276; Luo et al (1999) Nature Med 5(1), 1 17-122; Arcuturs Updates, for example June 1999 and February 1999; U.S. Pat. No. 5,859,699 (all incorporated herein by reference). The cells of interest are visualised, for example by immunohistochemical techniques, and transferred to a polymer film that is activated by laser pulses. The technique may also be used for isolation of cells which are negative for a particular component. Microscopes useful in performing LCM are manufactured by Arcturus Engineering, Inc., 1220 Terra Bella Avenue, Mountain View, Calif. 94042, USA.

LCM may be used with other isolation or enrichment methods. For example, LCM may be used following a method which enriches the sample for the target cell type.

In a further preferred embodiment, the level of said IRAK1 protein is measured. Preferably, the level of said protein is measured by contacting the protein with a molecule which selectively binds to said IRAK1 polypeptide. The sample containing protein derived from the patient is conveniently a sample tissue. It may be useful to measure the elevated level (tumour) versus lower level (normal) of the said IRAK1 polypeptide in some circumstances, such as when assessing breast tissue. The methods of the invention also include the measurement and detection of the said IRAK1 polypeptide in test samples and their comparison in a control sample.

The sample containing protein derived from the patient is conveniently a sample of the tissue in which cancer is suspected or in which cancer may be or has been found. Methods of obtaining suitable samples are described in relation to earlier methods and will be apparent to the skilled person. For example the sample may be any one of needle biopsy, core biopsy, nipple or lymph node aspirate. The sample may also be lymph node-derived material which may be particularly useful in determining whether a cancer has spread. Single cells may be analysed, as noted above. The methods of the invention involving detection of IRAK1 protein are particularly useful in relation to historical samples such as those containing paraffin-embedded sections of tumour samples.

The level of IRAK1 protein may be determined in a sample in any suitable way.

In another aspect of the present invention, there is provided a method for aiding in selecting a therapeutic strategy for a patient with breast cancer who is receiving paclitaxel therapy, or a patient who has previously received or is receiving paclitaxel therapy and has relapsed, the method comprising assessing the level of IRAK1 nucleic acid, protein or activity in a sample, and assessing the paclitaxel resistance status of the patient. By "paclitaxel resistance status" we include the meaning of a measure of the level of resistance to paclitaxel therapy that that patient's cancer cells may demonstrate. It is considered that this, in combination with a measure of IRAK1 activity may make for an informed treatment. The assessment of "paclitaxel resistance status" may be carried out for the first time in the patient, or may be implied from patient notes following past treatment of said patient with paclitaxel therapy, or possibly assessed previously by some other means. In addition to or as an alternative to assessing a patient's history of unresponsiveness to paclitaxel therapy, the "paclitaxel resistance status" may be assess by any known variety of means.

Preferably, if the level of IRAK1 nucleic acid, protein or activity in the sample is an elevated level; and if the patient is assessed as having an elevated paclitaxel resistance status or being resistant to paclitaxel therapy, then the selected treatment regime may comprise treating the patient with an inhibitor of IRAK1 activity. The inhibitor may be a ginsenoside.

In a further aspect of the present invention, it provides for a method for aiding in determining whether a patient with breast cancer has a relatively high or relatively low likelihood of disease free survival, the method comprising assessing the level of IRAK1 nucleic acid, protein or activity in a sample obtained from the patient. For example, a low IRAK1 level may be considered to indicate a >90% chance of cure with standard therapy, and a high level may be considered to indicate a <85% chance of cure. By "cure", it is meant to include at least 10 years of breast cancer free survival.

A further aspect of the present invention, there is provided a method for treating a patient with breast cancer, the method comprising administering an inhibitor of IRAK1 activity to the patient. In an embodiment, wherein the inhibitor is a ginsenoside.

In a further aspect of the present invention, there is provided a use of an inhibitor of IRAK1 activity in the manufacture of a medicament for treating a patient with breast cancer, wherein the level of IRAK1 nucleic acid or protein in a sample from the patient has been determined to be elevated. The breast cancer may be triple negative breast cancer.

In yet a further aspect of the invention, there is provided a kit of parts useful for assessing breast cancer comprising: (a) an agent which is specifically capable of use in determining the level of IRAK1 protein in a sample; and (b) means for separating breast cells from a sample, or identifying breast cells in a sample in order to carry out the IRAK1 assay.

Preferably, the agent is a nucleic acid which selectively hybridises to IRAK1 nucleic acid, or is a molecule which selectively binds to IRAK1 protein.

In another aspect of the present invention, there is provided a screening method for identifying a compound likely to be useful in treating breast cancer, the method comprising: (a) determining the effect of a test compound on IRAK1 nucleic acid, protein or activity level; and (b) selecting a compound that reduces said level.

Preferably, the test compound is determined in vitro, or in a breast cancer cell line.

Metastasis and tumor relapse remain the major clinical challenges for aggressive breast cancer therapy. Advantageously, here, we report that interleukin 1 receptor associated kinase 1 (IRAK1) is overexpressed in a subset of breast cancers in particular triple negative breast cancer (TNBC), where it acts to drive aggressive growth, metastasis and acquired resistance to chemotherapy. High level of IRAK1 expression in TNBC confers susceptibility of NF-κB-related cytokine secretion and aggressive growth to genetic and pharmacologic inactivation of IRAK1. Moreover, metastatic TNBC shows increased IRAK1 expression and gain of IRAK1-dependency for invasion and metastasis. Importantly, chemotherapy activates IRAK1 signaling, contributing to increased cancer stem cell enrichment and acquired resistance to chemotherapy. Pharmacologic inhibitors of IRAK1, including a traditional oriental medicine derivative, are able to reverse chemoresistance by trigging massive apoptosis through inhibiting p38-MCL1 pathway. The present invention thus provides evidence that IRAK1 may be used as a therapeutic target for restricting refractory TNBC progression and improving the efficacy of current chemotherapy.

The present invention also aims to validate the association of phosphoryated IRAK1 (p-IRAK1) with clinical outcome, and to evaluate its potential as a marker of response to alternate non-cross resistant agents and IRAK1 inhibition in paclitaxel-resistant TNBC. We have described a role of IRAK1 in breast tumour growth and metastasis. Here, we also validate the correlation between tumour p-IRAK1 levels and outcome in two independent cohorts of TNBC. Thresholds for a positive p-IRAK1 result will be determined. We are particularly interested in whether p-IRAK1 levels in the residual tumour after neoadjuvant chemotherapy predict paclitaxel resistance and for recurrence. This will be evaluated first in archival samples, and then in prospectively collected samples obtained from women with TNBC tumours treated with taxane-based chemotherapy.

We also looked at initial results that suggested a therapeutic role of p-IRAK1 in TNBC. Having observed activation of IRAK1 signaling in acquired paclitaxel resistance, we will further explore the response of p-IRAK1-overexpressing (paclitaxel resistant) tumours to alternate non-cross resistant agents cisplatin and gemcitabine, and the novel IRAK1 inhibitor, pacritinib. Efficacy studies were carried out in a series of TNBC cell lines representative of the TNBC subtypes and then in mouse xenografts, to determine if response varies among the different subtypes, and if response to either of the three agents can be stratified according to p-IRAK1 levels. This is important in defining the clinical scenarios for the optimal use of each agent. Finally, these findings were verified in TNBC PDX models. Paclitaxel resistant xenografts will either be generated from residual tumour post-paclitaxel neoadjuvant chemotherapy (obtained from the surgical specimen), or from treatment naïve TNBC treated with paclitaxel in vivo. These experiments will provide important data on how paclitaxel-resistant tumours will be expected to respond to cisplatin, gemcitabine and pacritinib in the clinical setting.

The present invention potentially improves outcomes in those with residual TNBC after neoadjuvant chemotherapy. Already, there is evidence that targeting residual tumours will improve survival. Here, our protocol follows a concept similar to the Phase III EA1131 trial, but with the major advantage that p-IRAK1 can be detected with IHC, making it more affordable and more widely applicable. Single gene markers are not necessarily inferior to multi-gene assays; to this day, ER, PR and HER2 are the only biomarkers widely used in routine clinical practice. Furthermore, IRAK1 inhibition has potential as a novel therapeutic, particularly valuable in TNBC tumours that fail first-line taxane-based regimens. In addition, p-IRAK1 can also be used to guide the choice of chemotherapy in the adjuvant and metastatic settings. Evaluation of the tumour prior to surgery to predict chemotherapy response circumvents the problem of not having any gross disease to monitor in the adjuvant setting. In metastatic tumours that are often heavily treated and which inevitably acquire resistance and progress, p-IRAK1 can determine whether cisplatin, gemcitabine and even pacritinib are viable alternatives.

In order that the present invention may be fully understood and readily put into practical effect, there shall now be described by way of non-limitative examples only preferred embodiments of the present invention, the description being with reference to the accompanying illustrative figures.

In the Figures:

FIG. 1. IRAK1 overexpression in breast cancers (A) TCGA analysis shows the expression levels of IRAK family members across different subtypes of breast cancers and normal tissues. Normal, n=22; Basal-like, n=98; Luminal A, n=232; Luminal B, n=129; HER2, n=58. (*p<0.05, *p<0.001, **p<0.0001, n.s, not significant, Tukey's multiple comparisons test). (B) IHC analysis of IRAK1 protein expression in different subtypes of breast cancers. Shown are representative IHC images of IRAK1 expression (left) and quantifications (right). (C) Kaplan-Meier analyses of relapse free survival, overall survival and distant metastasis free survival of breast cancer patients from the KM plotter dataset. Patients were stratified into "low" and "high" IRAK1 expression based on the median IRAK1 mRNA expression.

Figure 2:
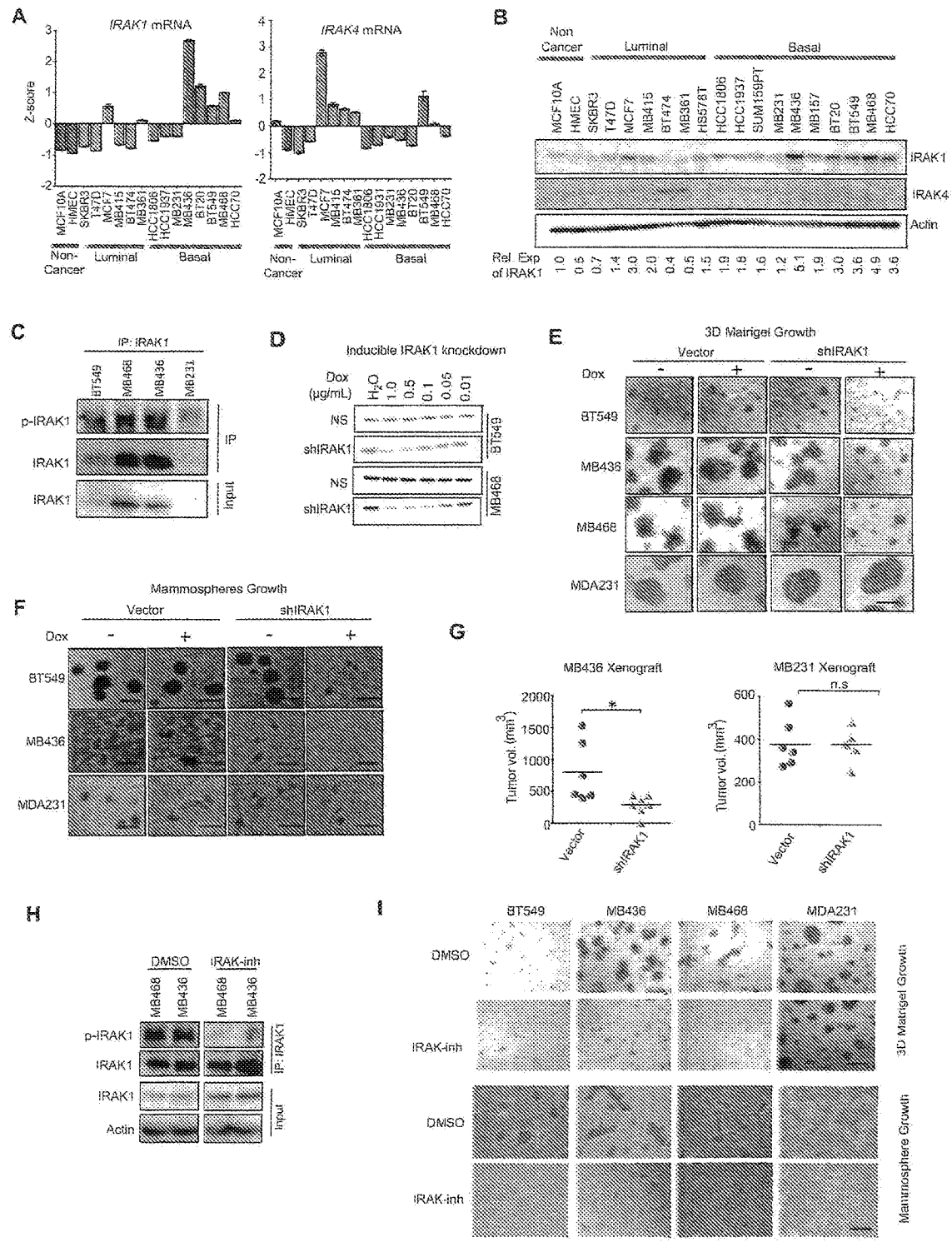

FIG. 2. IRAK1 knockdown and pharmacologic inhibition impair the aggressive growth phenotypes of TNBC cells (A) qRT-PCR analysis of IRAK1 and IRAK4 expression in a panel of breast cancer cell lines. (B) Western blot analysis of IRAK1 and IRAK4 expression. Below shows the densitometric quantification of IRAK1 expression relative to MCF10A. (C) Western blot analysis of immunoprecipitated IRAK1 for phosphorylation (T209) in indicated TNBC cell lines. (D) Western blot showing the knockdown efficiency of inducible IRAK1 (shIRAK1) or non-specific shRNA (NS) with or without doxycycline (Dox) treatment. (E&F) 3D Matrigel and mammosphere growth of indicated TNBC cells treated with and without Dox (0.51 μg/mL) for 7 days. Scale bars, 100 μm. (G) Scattered plot showing the MB436 and MDA231 xenograft tumor growth for 36 days in female NOD/SCID mice carrying cells non specific shRNA vector control (n=6) or shIRAK1 (n=6). (H) Western blot showing the effects of IRAK-inh (5 μM) on p-IRAK1 (T209) in immunoprecipitated total IRAK1. (I) Effects of IRAK-inh (5 μM) on 3D Matrigel growth and mammosphere formation, Error bars represent mean±SEM, n=3. $*p<0.05$, ns, not significant.

Figure 3:
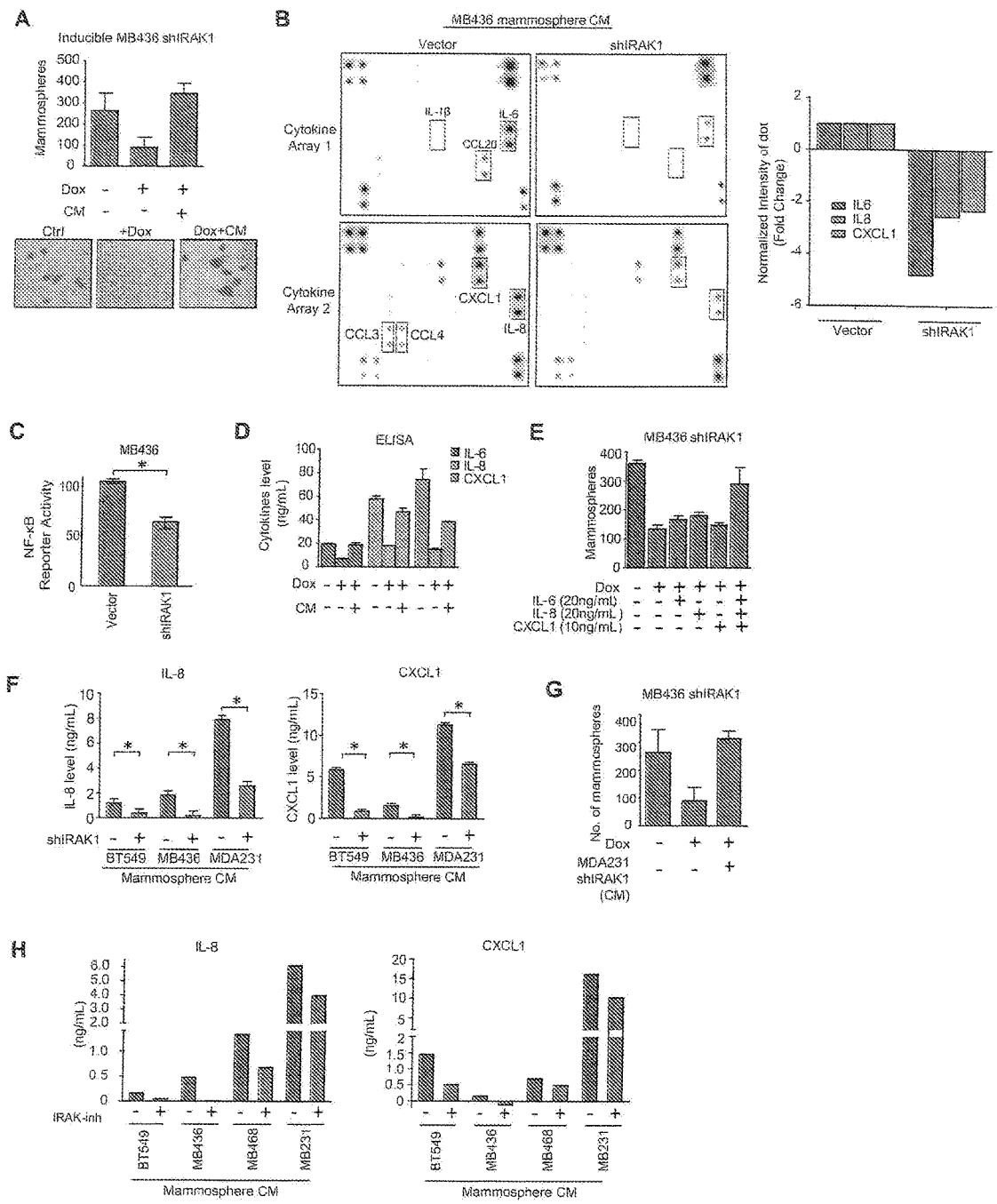

FIG. 3. IRAK1-dependent cytokine secretions are required for mammosphere formation (A) Mammosphere formation of MB436 shIRAK1 cells treated with and without Dox (0.5 μg/ml) for IRAK1 knockdown. CM, conditioned medium from mock-treated MB436 shIRAK1 cells. Quantifications (top) and representative images (bottom). Scale bars, 100 μm. (B) Cytokine Antibody Array profiling of cytokine secretions in the growth medium of MB436 cells expressing vector control or shIRAK1 in the presence of Dox (left). Quantifications of IL6, IL8 and CXCL1 changes in shIRAK1 cells relative to the vector control cells (right). (C) NF-κB luciferase reporter activity in indicated MB436 cells in the presence of Dox. (D) ELISA assay showing the secretion of IL-6, IL-8 and CXCL1 in MB436 shIRAK1 cells with or without Dox or conditional medium from mock-treated cells. (E) Mammosphere formation assay in the presence of Dox or recombinant cytokines individual or in combination as indicated. (F) ELISA assay showing the secretion of IL-8 and CXCL1 in indicated TNBC cells expressing vector control or shIRAK1. (G) Mammosphere formation of MB436 shIRAK1 cells treated with Dox alone or together with conditioned medium (CM) from MDA231 shIRAK1 cells. (H) Effects of IRAK-inh (5 μM) treatment on cytokine secretions of indicated TNBC cells. Error bars represent mean±SEM, n=3. $*p<0.05$.

Figure 4:
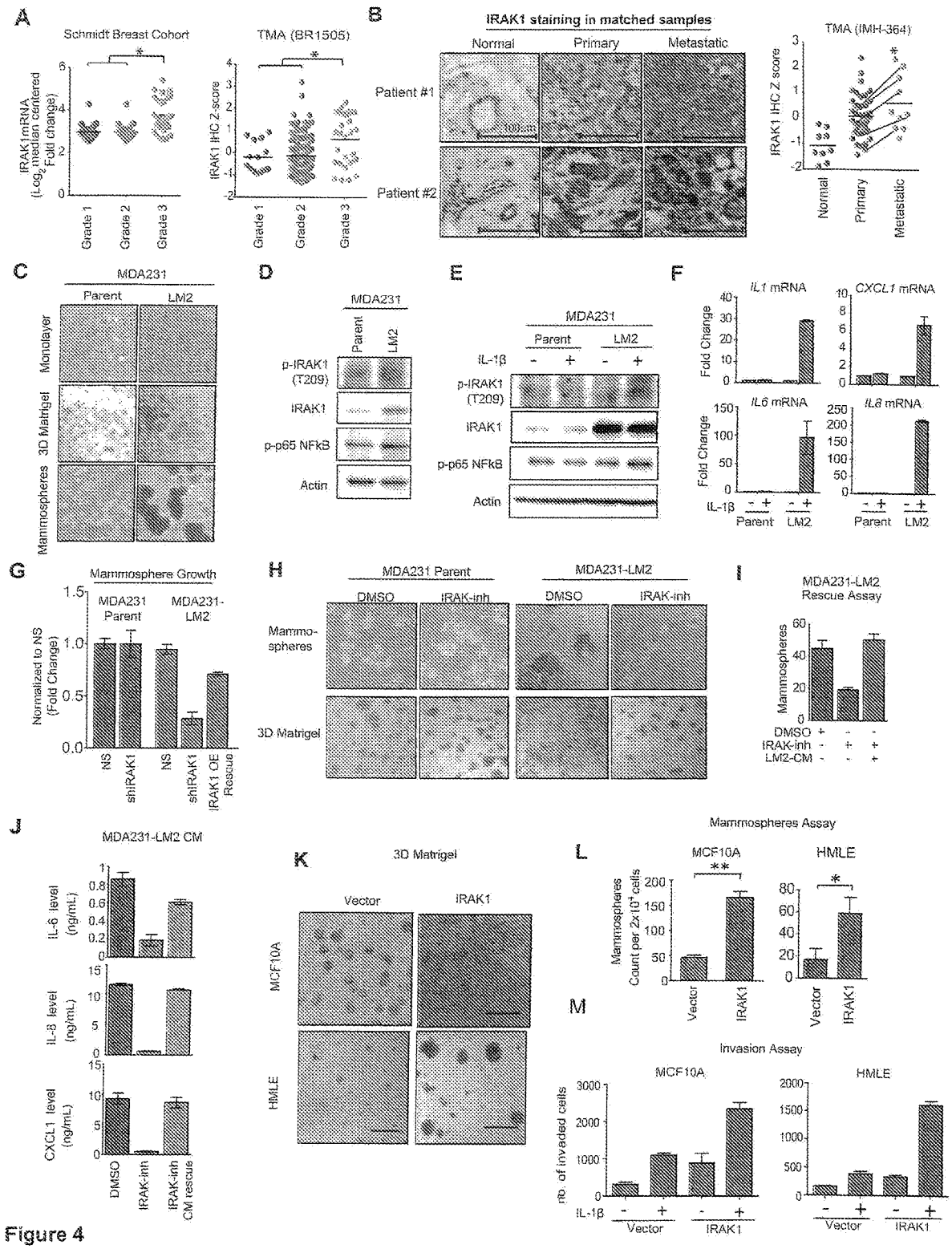

FIG. 4. TNBC metastasis shows increased IRAK1 expression/activity and IRAK1-dependency (A) Scatter plots showing the IRAK1 mRNA levels in Schmidt Breast Cohort (GSE11121) composed of 200 breast cancer tumors of different clinical grades (Grade 1, n=29; Grade 2, n=136; Grade 3, n=35) (left), and IRAK1 IHC staining results in TMA-BR1505 with 150 breast tumor cores of different clinical grades (Grade 1, n=14; Grade 2, n=104; Grade 3, n=28) (right). (B) Representative IHC images of IRAK1 protein expression in matched normal, primary and metastatic tumors from two patients (left). Scatter plot showing IRAK1 protein expression in TMA-IMH364, including 9-paired primary and matched metastatic tumors ad indicated by the black lines (right). (C) Phase contrast microscopic images of MDA231 parental and MDA231-LM2 cells cultured in monolayer, mammospheres and 3D Matrigel conditions. Scale bars, 100 μm. (D) Western blot showing the expression of indicated proteins. (E) Western blot showing the expression of indicated proteins in the absence or presence of IL-1β (10 ng/ml) for 24 hours. (F) qPCR analysis showing the relative expression of indicated cytokines in cells treated in (E). (G) Mammosphere formation assay of MDA231 and MDA231-LM2 cells expressing vector, shIRAK1, or together with ectopic IRAK1 for rescue. (H) Representative phase contrast images in mammosphere and 3D Matrigel gel, treated with or without IRAK-inh (5 μM) for 7 days. (I) Mammosphere growth of MDA231-LM2 cells treated with 5 μM IRAK-inh, with and without adding conditioned medium (CM) from mock-treated MDA231-LM2 cells. (J) ELISA quantification of indicated cytokine levels in (I). (K) 3D Matrigel growth of MCF10A and HMEL cells expressing vector or ectopic IRAK1. scale bars, 100 μM. (L) Mammosphere assay of cells in (K). (M) Invasion assay of cells in (K) treated with recombinant IL-1b (10 ng/ml) for 3 days. $*p<0.05$, $**p<0.01$.

Figure 5:
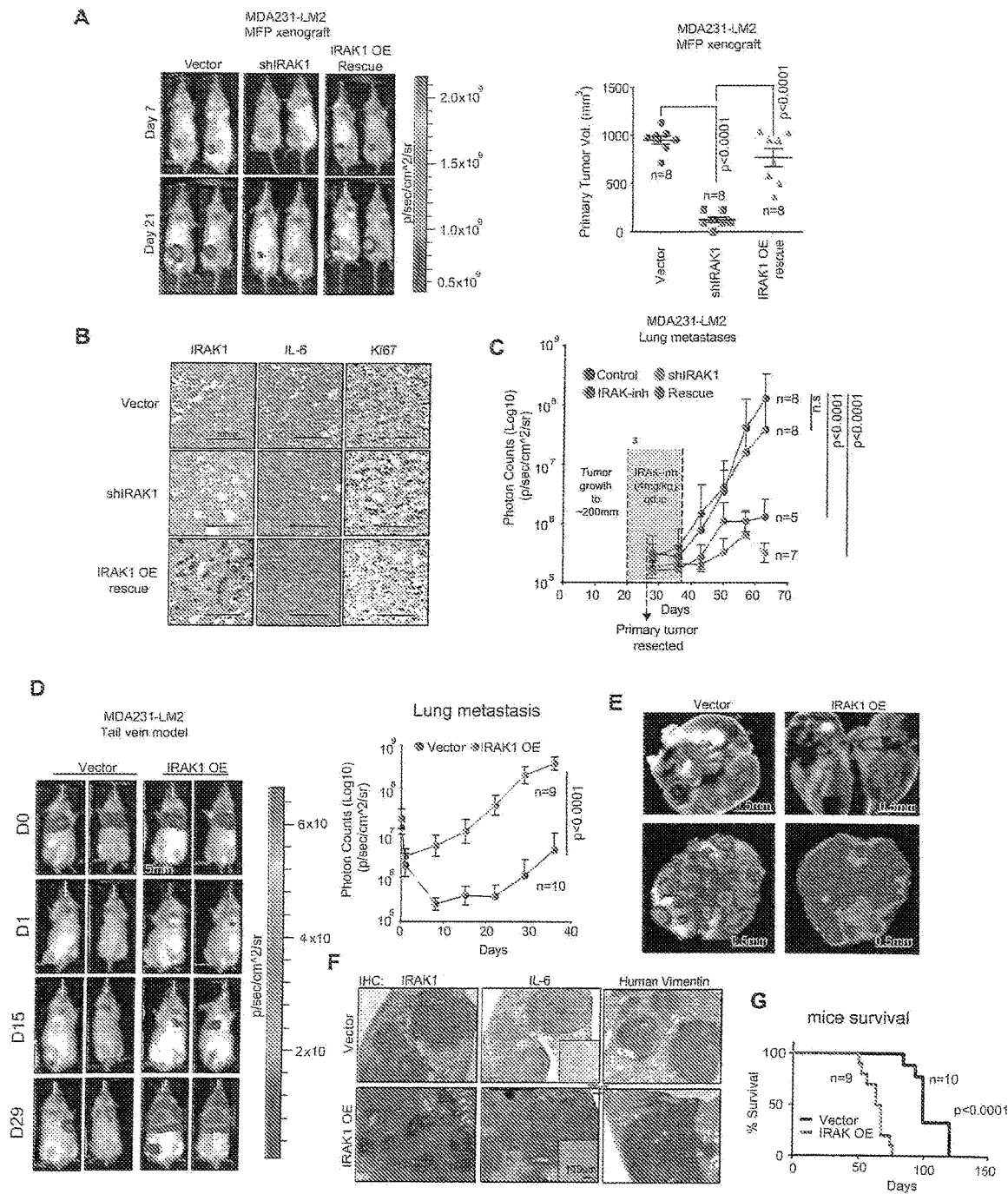

FIG. 5. IRAK1 is both required and sufficient to promote TNBC growth and metastasis in vivo (A) Representative Bioluminescent imaging (BLI) showing the mammary fat pad (MFP) xenograft tumor growth of indicated MDA231-LM2 cells in NOD/SCID mice (left). Scatter plot showing the tumor volumes at day 27. (B) Representative IHC staining of indicated proteins on xenograft tumors harvested in (A). (C) BLI curves showing the development of lung metastasis of MDA231-LM2 cells in (A), or treated with IRAK-inh (4 mg/kg, qd, ip) for 14 days. Primary tumors were surgically removed at day 21. IRAK-inh treatment started 7 days before the primary tumor removal. (D) Representative BLI images of NOD/SCID mice and BLI curves showing the lung metastases from D0 to D29, derived from lateral tail vein injection of indicated MDA231-LM2 cells. (E) Whole lung staining showing the metastatic nodules (upper) and ex vivo BLI of lung metastasis (below) of representative mice at 6 weeks postinjection. (F) IHC staining of indicated proteins in lung tissues in (E). (G) Kaplan-Meier survival curves of mice from (E). n=8. P values denotes Log-Rank (mantel-Cox) test.

Figure 6:
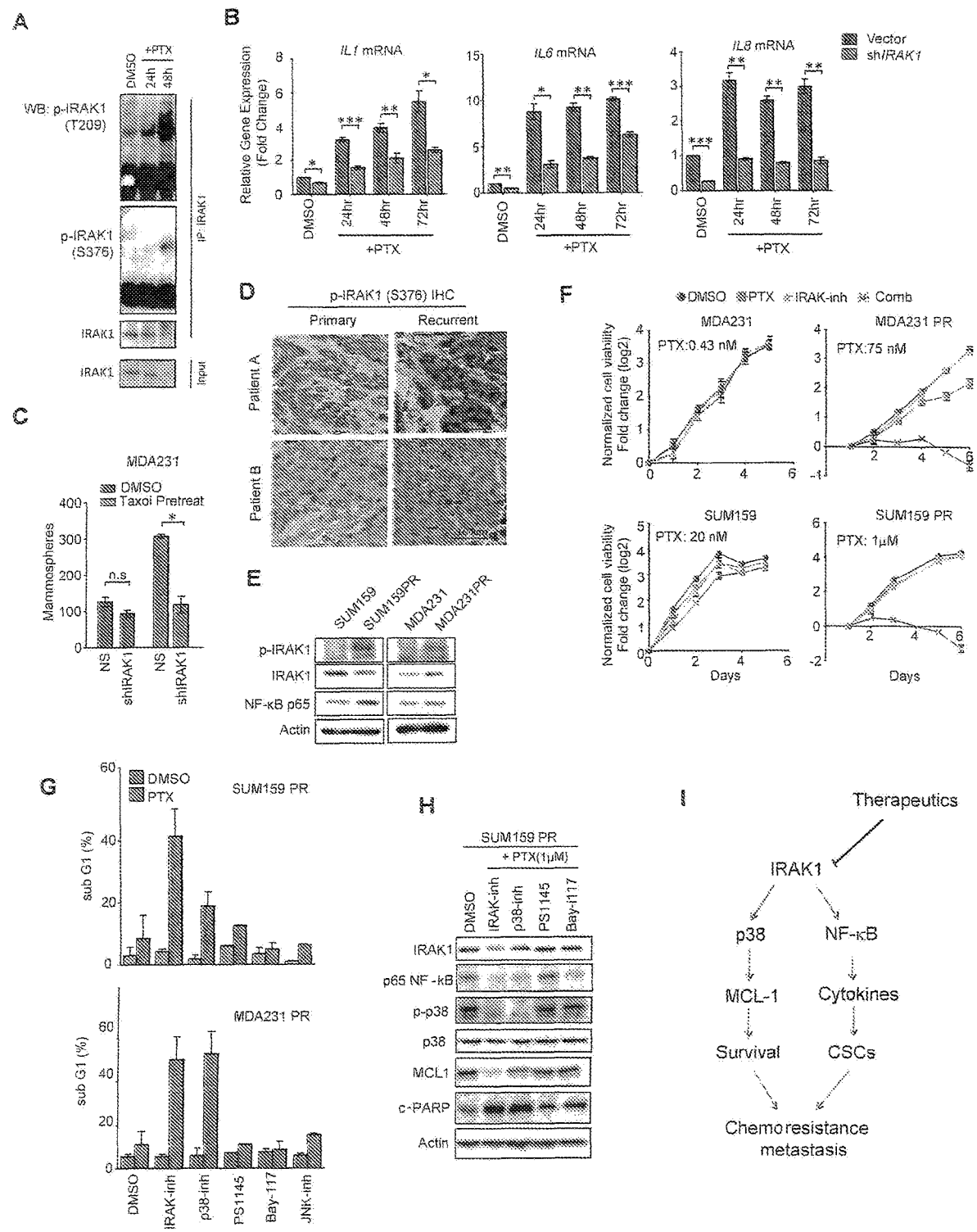

FIG. 6. Role of IRAK1 signaling in acquired resistance to chemotherapy.

(A) Western blot showing the p-IRAK1 of immunoprecipitated IRAK1 in MDA231 cells treated with 5 nM Paclitaxel (PTX) for 24 and 48 hours. (B) qRT-PCR analysis of indicated cytokine mRNAs in cells treated with 5 nM PTX for indicated times. (C) Mammosphere formation assay of MDA231 expressing vector or shIRAK1 cells after PTX (10 nM) pre-treatment for 96 hours in monolayer. PTX treated cells were then washed and the viable cells were seeded for mammosphere assay. (D). IHC analysis of p-IRAK1 (S376) in two paired clinical primary and recurrent breast tumors after chemotherapy. (E) Western blot shows the indicated proteins in MDA231 and SUM159 parental and Paclitaxel-resistant sublines (PR). (F) Cell viability of parental and resistant sublines treated with pre-determined subtoxic doses of Paclitaxel (PTX) as indicated, 5 μM IRAK-inh, or combination. (G) Apoptosis as determined by FACS analysis of Sub-G1 cells in SUM159-PR (top) and MDA231-PR (bottom) cells treated with Paclitaxel, together with or without indicated small molecule inhibitors of IRAK1, p38, JNK, or IKKβ/NF-κB (PS1145 and Bay117082). (H) Western blot shows the indicated molecular signaling events in cells SUM159-PR cells treated in (G). (I) Schematic summarizing the roles of IRAK1 in driving metastasis and chemoresistance in TNBC. Error bars represent mean±SEM, n=3. $*p<0.05$, $P<0.01$, $*P<0,001$.

Figure 7:
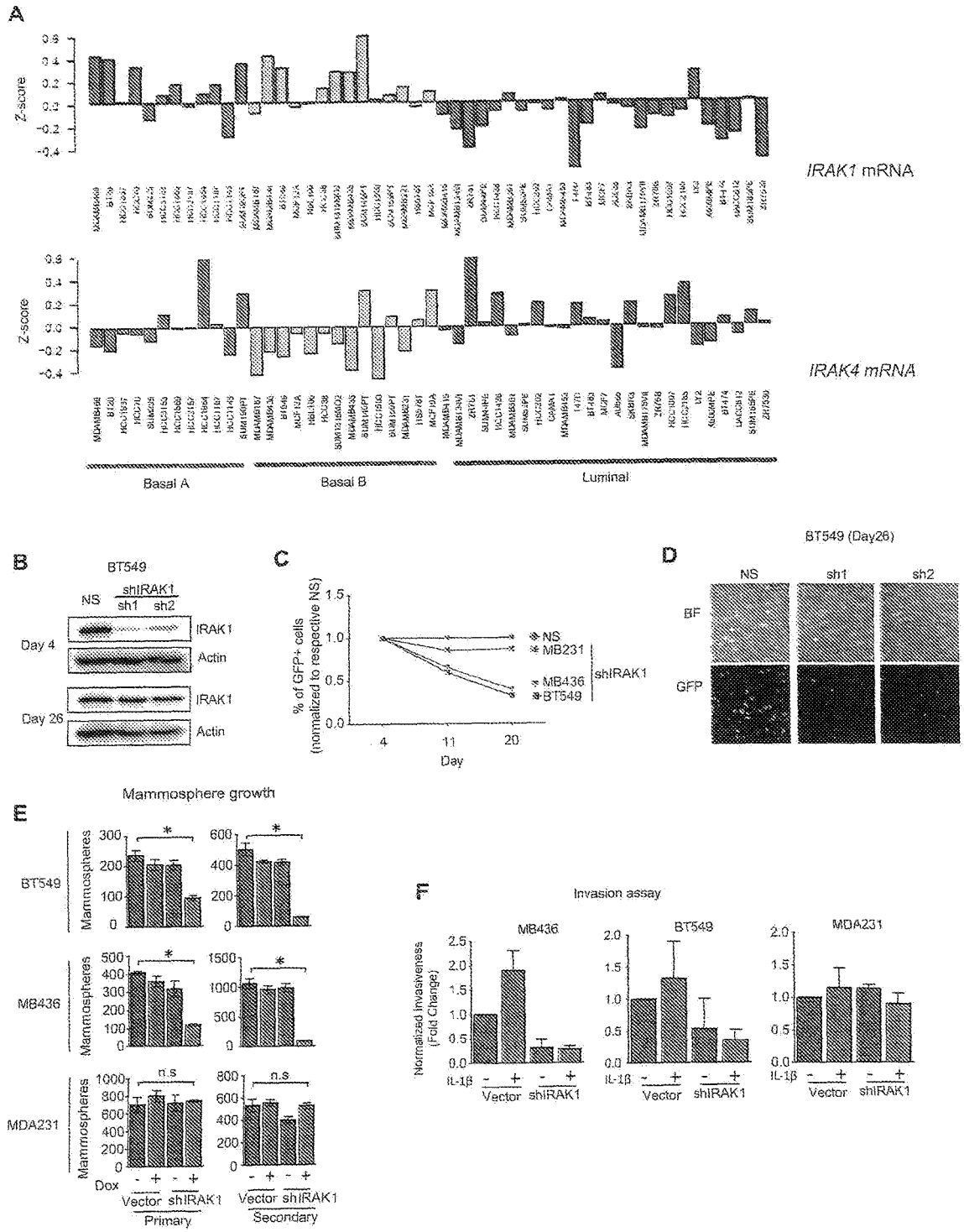

FIG. 7. IRAK1 knockdown impairs aggressive growth of TNBC cells (A) Expression profiles of IRAK1 and IRAK4 mRNAs in 51 breast cancer cell lines using the GOBO database. (B) Western blot showing IRAK1 expression in BT549 cells expressing non specific vector control (NS) or shIRAK1 sequence 1 and 2 (sh1 and sh2). (C) Percentage of GFP positive cells over time in TNBC expressing control (NS) or shIRAK1. (D) Microscope images of indicated BT549 cells at day 26. (E) Quantifications of primary and secondary mammosphere formation in TNBC cells treated with Dox to induce IRAK1 knockdown. (F) Invasion assay of TNBC cells in response to IL-1β treatment for 3 days. Error bars represent mean±SEM, n=3. * P<0.05.

Figure 8:
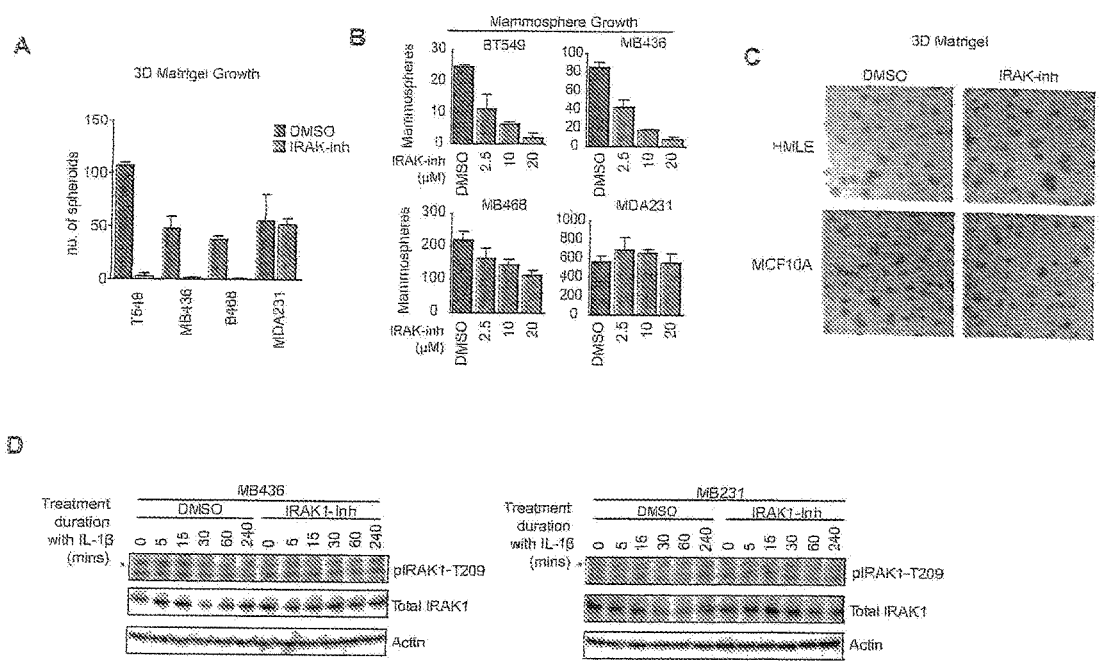

FIG. 8. Effects of IRAK1-inhibitor treatment on TNBC (A &B) Quantifications of 3D Matrigel and mammosphere growth treated with 5 µM IRAK-inh for one week. (C) Representative phase contrast microscopy images of 3D matrigel growth assay showing the morphology of non-cancerous MCF10A and HMLE cell lines after one week of IRAK-inh (5 uM) treatment. (D) Western blot analysis of total and p-IRAK1 at indicated time points after IL-1β and IRAK-inh (5 uM) treatment on MB436 and MDA231 cell lines.

Figure 9:
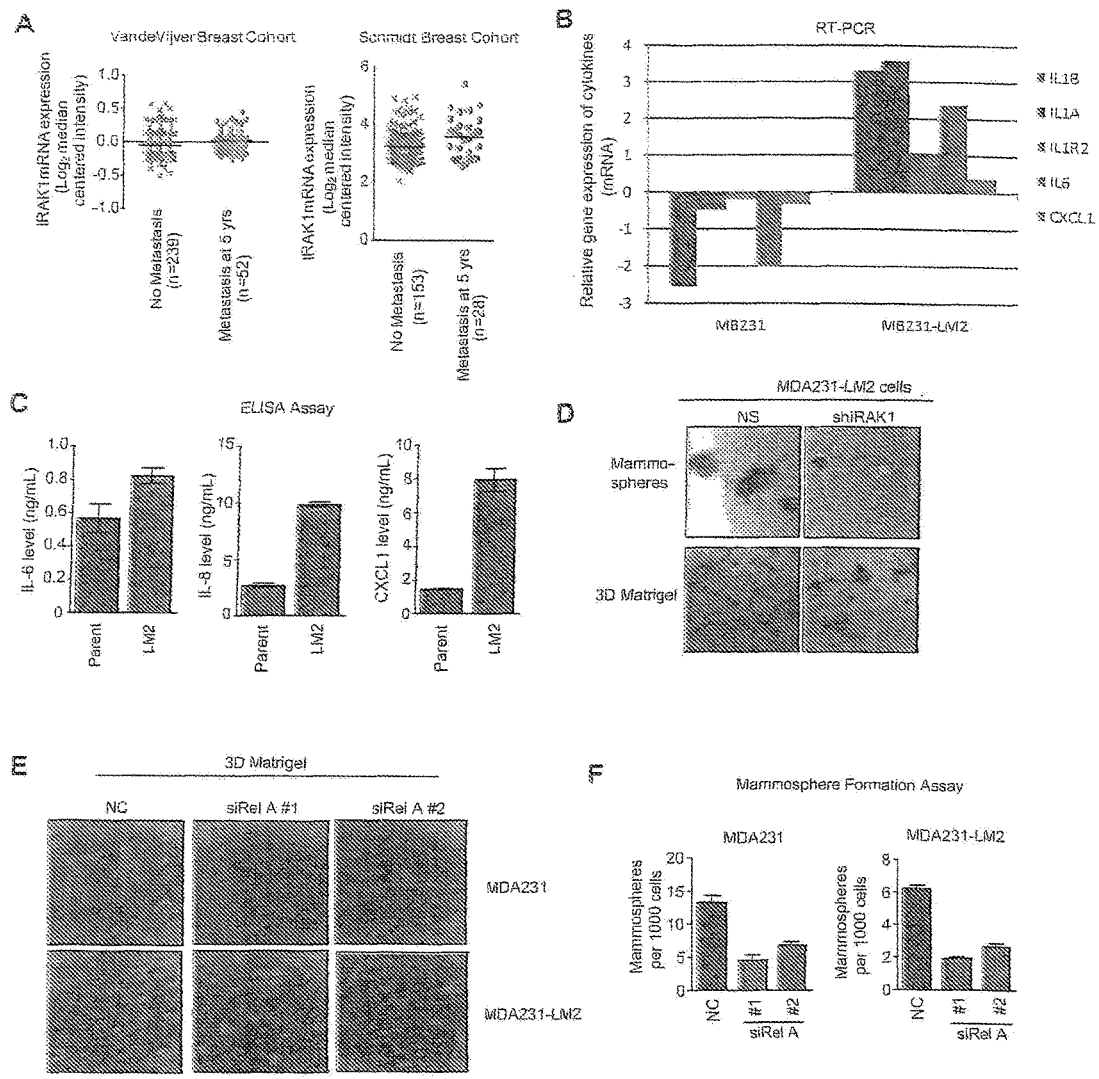

FIG. 9. TNBC metastatic cells shows increased IRAK1 signaling and IRAK1-dependency.

(A) Stratified analysis of Van de Vijver Breast Cohort (left) and Schmidt Breast Cohort correlating IRAK1 levels with 5-year metastasis incidence in breast cancer patients. (B) q-PCR analysis of indicated cytokines mRNAs in MDA231 and MDA231-LM2 cells. (C) ELISA assay of indicated cytokine levels in conditioned medium of MDA231 and MDA231-LM2 cells. (D) 3D Matrigel and mammosphere growth of MDA231-LM2 cells expressing NS or shIRAK1. (E and F) 3D Matrigel and mammosphere formation assay of MDA231 and MDA231-LM2 cells after RelA knock down.

Figure 10:
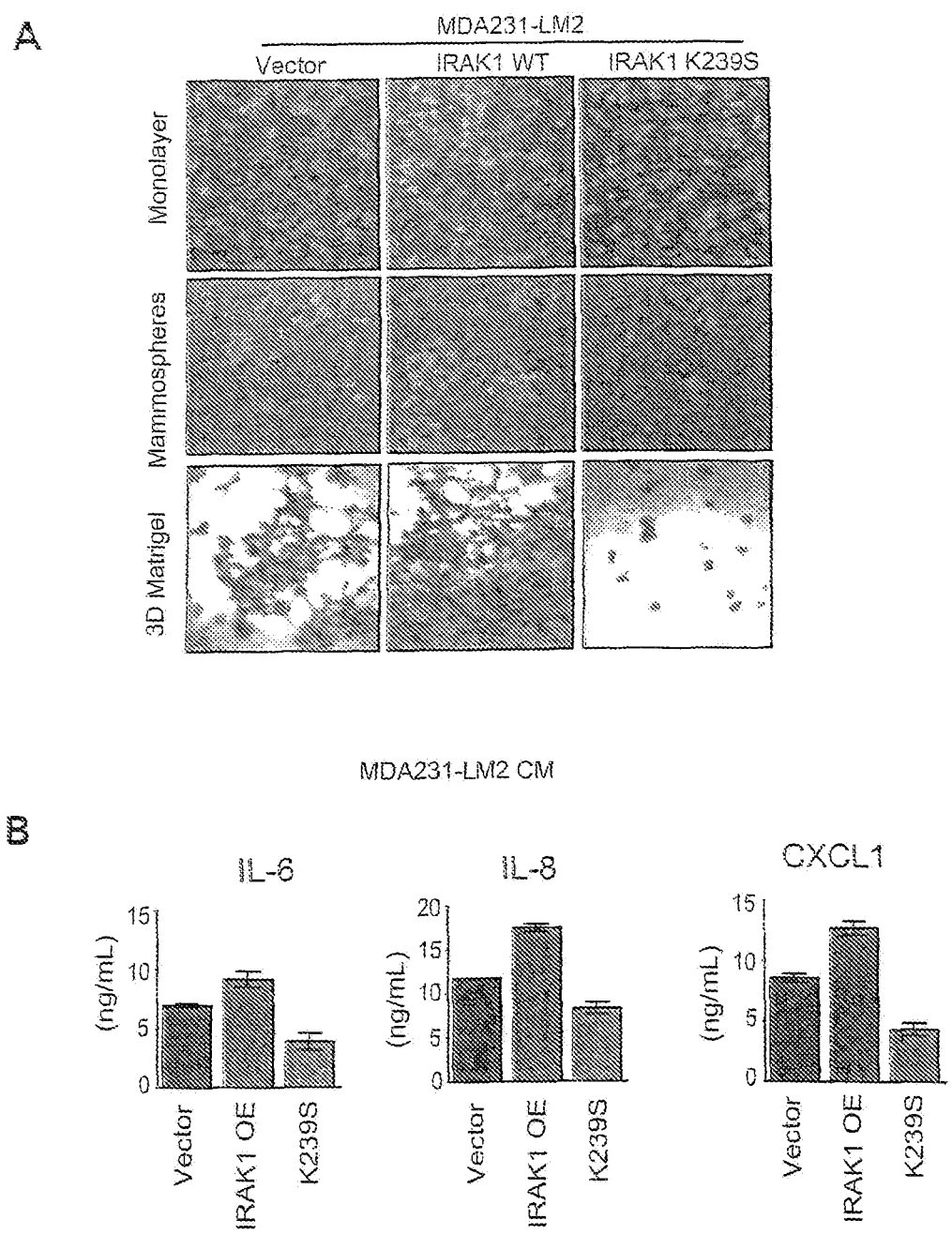

FIG. 10. IRAK1 kinase activity is required for the growth of metastatic MDA231-LM2 cells (A) Monolayer, 3D Matrigel and mammosphere growth of MDA231-LM2 cells expressing vector, ectopic IRAK1 and kinase-dead mutant IRAK1. (B) ELISA assays of indicated cytokines in MDA231-LM2 cells in (A).

Figure 11:
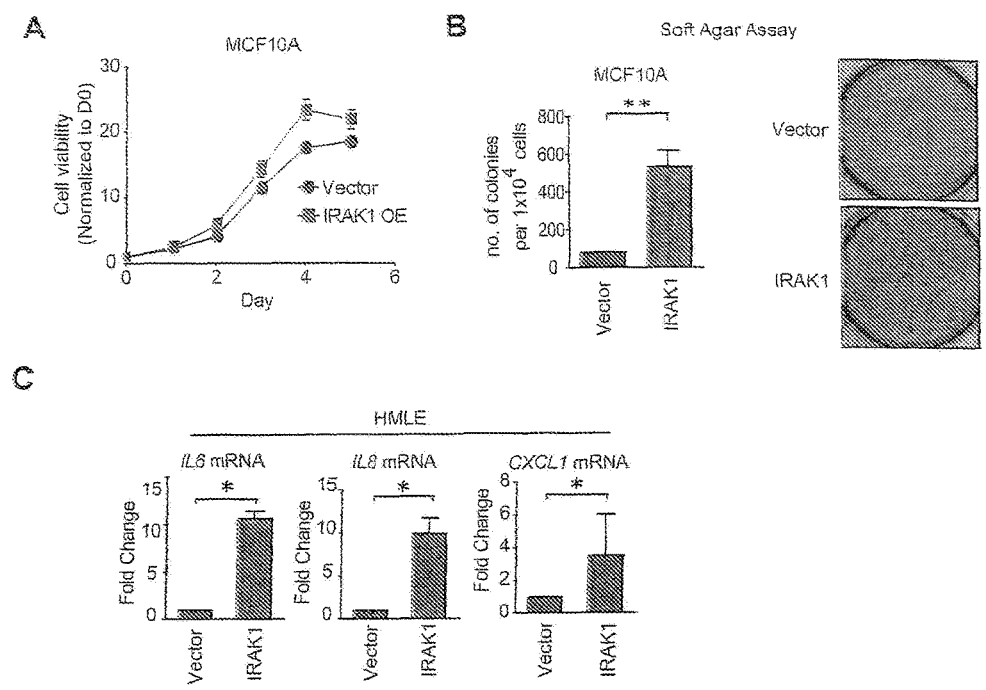

FIG. 11. Ecotopic IRAK1 is sufficient to drive aggressive growth of non-cancerous mammary epithelial cells.

(A) Cell proliferation of MCF10A cells overexpressing either the empty vector or ectopic IRAK1. (B) Soft agar assay. C) qRT-PCR analysis of IL6, IL8 and CXCL1 mRNAs. **P<0.05, Error bars represent mean±SEM, n=3.

Figure 12:
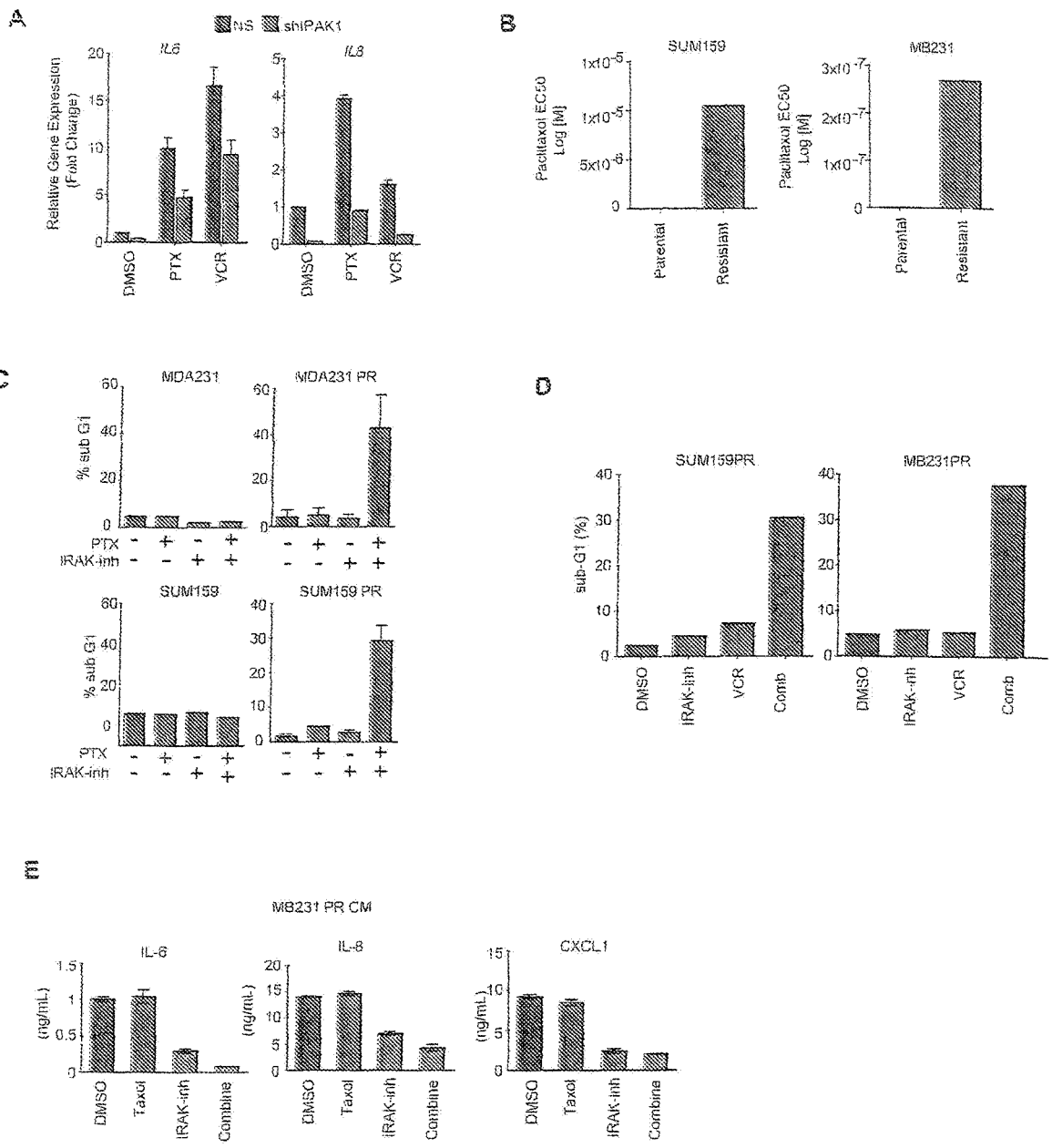

FIG. 12. IRAK1 signaling in acquired resistance to chemotherapy (A) qRT-PCR analysis of indicated cytokine mRNAs in MDA231 cells treated with Paclitaxel (PTX) and Vincristine (VCR) for 3 days. (B) Bar graphs showing the $EC_{50}$ of Paclitaxel in MDA231 and SUM159 cells parental and Paclitaxel resistant lines (PR). (C) Apoptosis as determined by FACS analysis of cells in Sub-G1, treated with PTX, IRAK-inh or both. (D) Apoptosis in PTX resistant cells treated with VCR, IRAK-inh or both. (E) ELISA assay of indicated cytokines in MDA231-PR cells as treated. Error bars represent mean±SEM, n=3.

Figure 13:
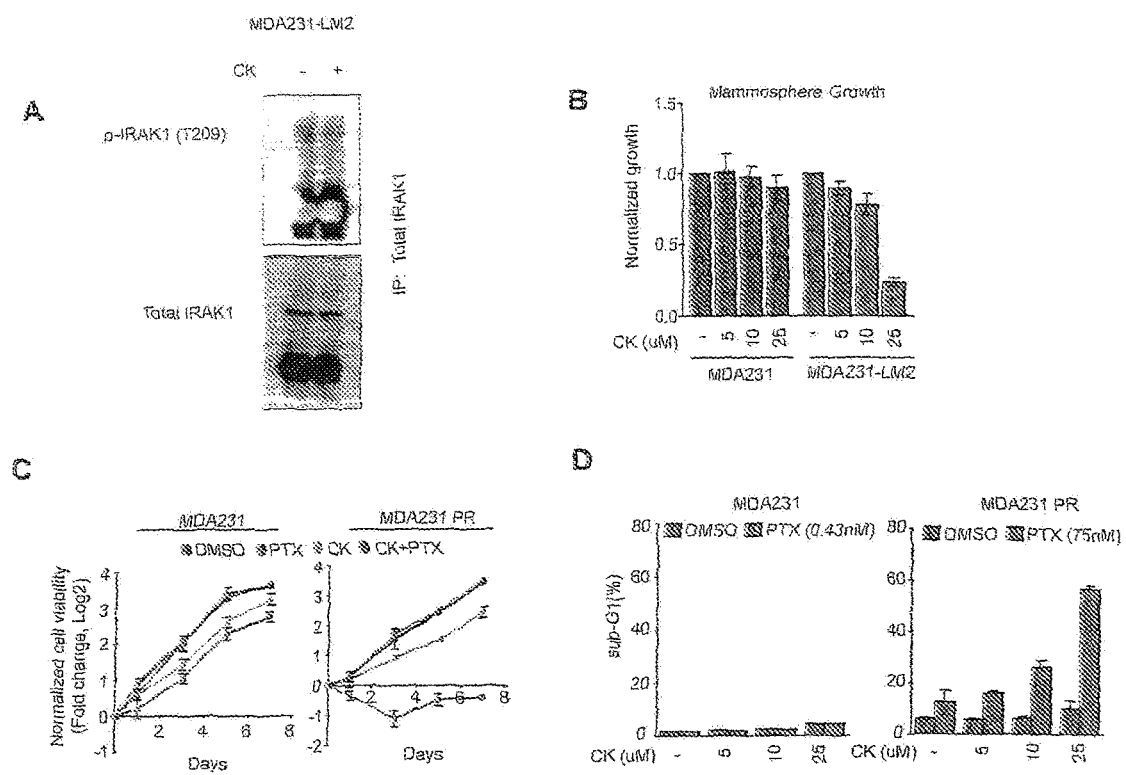

FIG. 13. Effects of Ginsenoside CK compound on TNBC (A). Western blot showing the effect of CK (25 µM) on p-IRAK1 of MDA231-LM2 cells. (B) Effects of CK on mammosphere growth of MDA231 and MDA231-LM2 cells. (C) Cell viability assay showing the effect of CK in combination with PTX in MDA231 and MDA231-PR cells. (D) Apoptosis of cells treated in (C).

Figure 14:
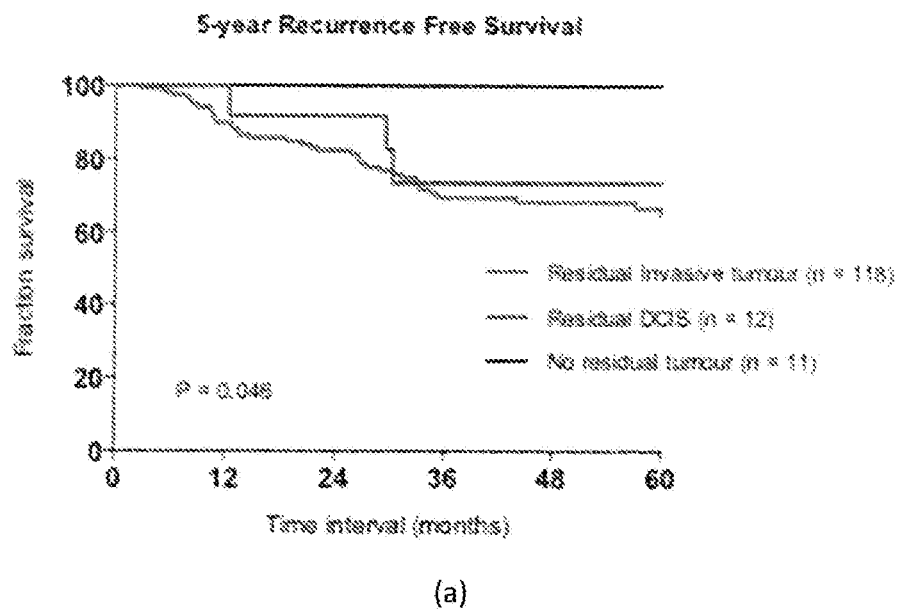
Figure 14:
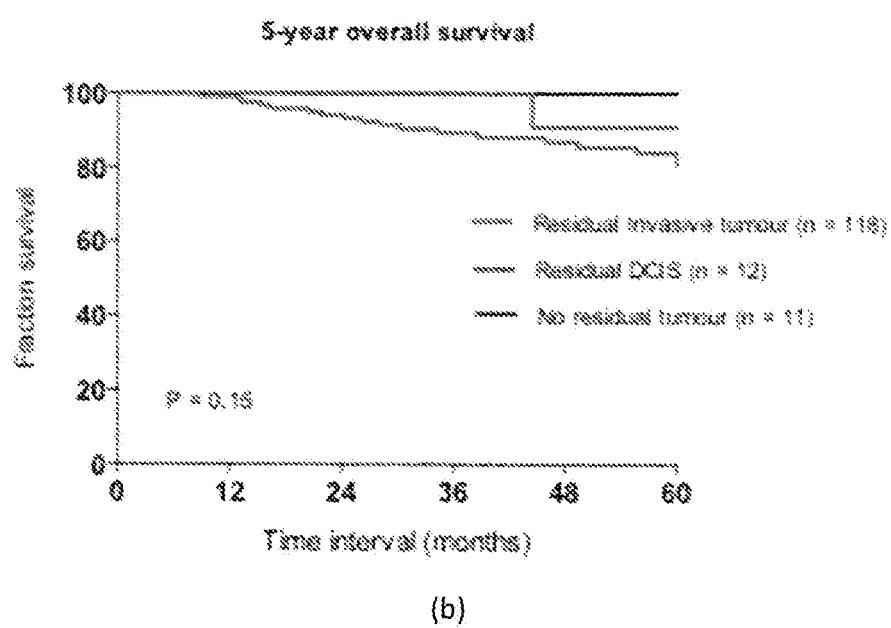

FIGS. 14 (a) and (b). Kaplan Meier survival curves of 5-year recurrence free and overall survival stratified by pathological response after neoadjuvant chemotherapy.

Figure 15:
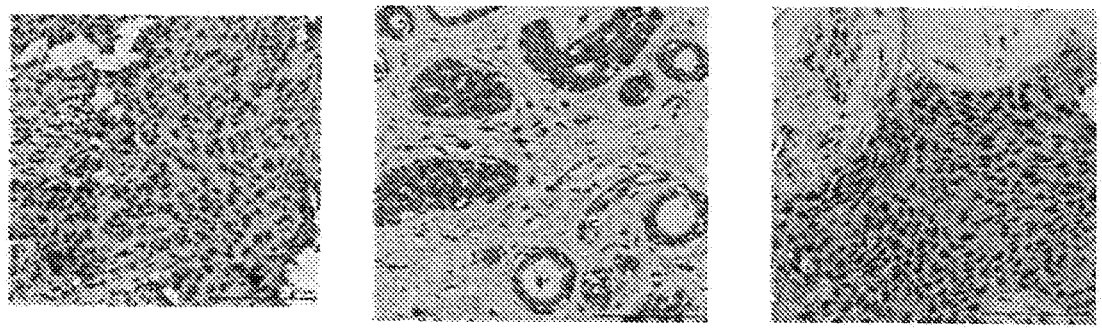
Figure 15:
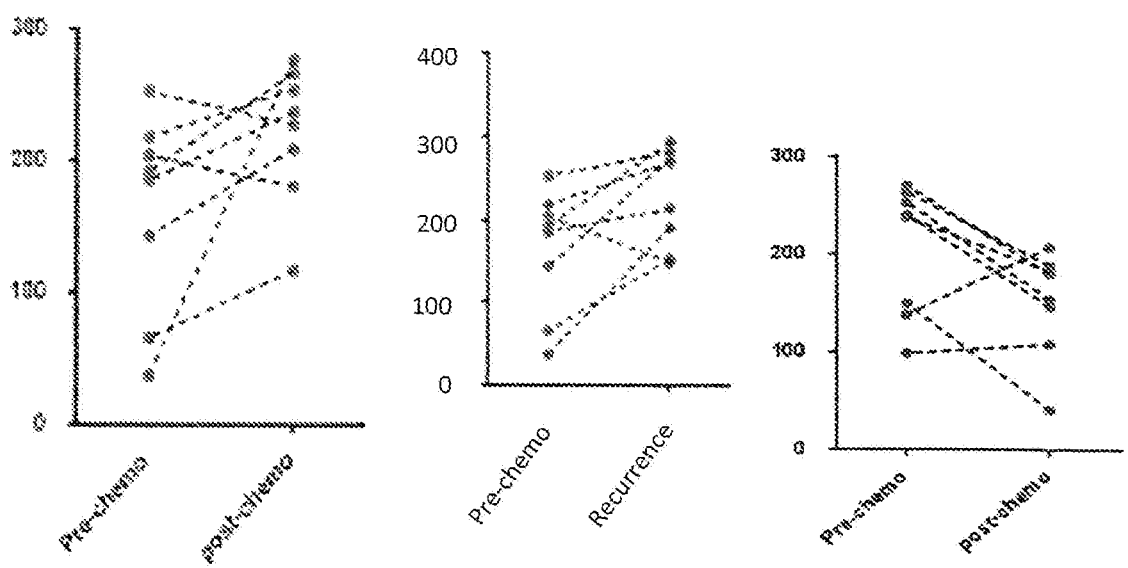

FIG. 15 (a). IHC analyses showing increase in positive p-IRAK1 staining in the pre-treated sample (left), residual tumour after chemotherapy treatment (centre) and the recurrent tumour (right) in the same patient.

FIG. 15 (b). Graphical representation of p-IRAK1 H scores in 8 patients with ER-negative tumours who developed recurrence. H scores of pre-treated and post-chemotherapy samples (P=0.04) (Left); H scores of pre-treated samples and recurrent tumours (P=0.05) (Right). C. Graphical representation of p-IRAK1 H scores in another 8 patients with ER-negative tumours without recurrence (P=0.05).

Figure 16:
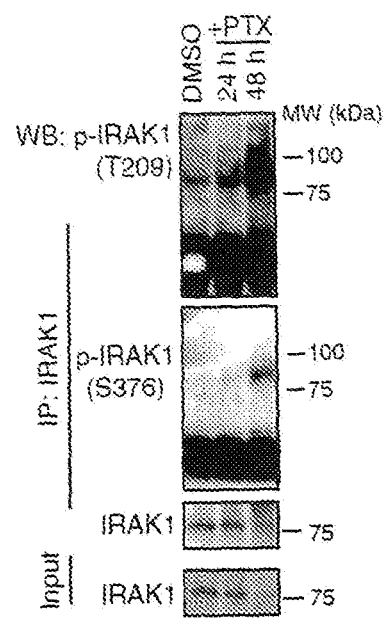
Figure 16:
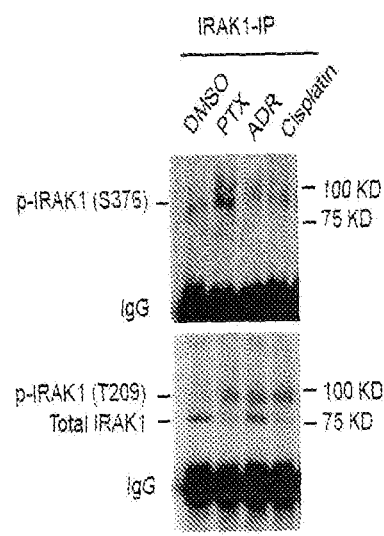

FIG. 16. Western blot of p-IRAK1 of immunoprecipitated IRAK1 in MDA231 cells treated with paclitaxel (PTX), doxorubicin (ADR), Cisplatin. (a). Induction of p-IRAK1 after PTX (5 nm). (b). Induction of p-IRAK1 when treated with PTX but not with ADR (2 µM) or Cisplatin (5 µM).

Figure 17:
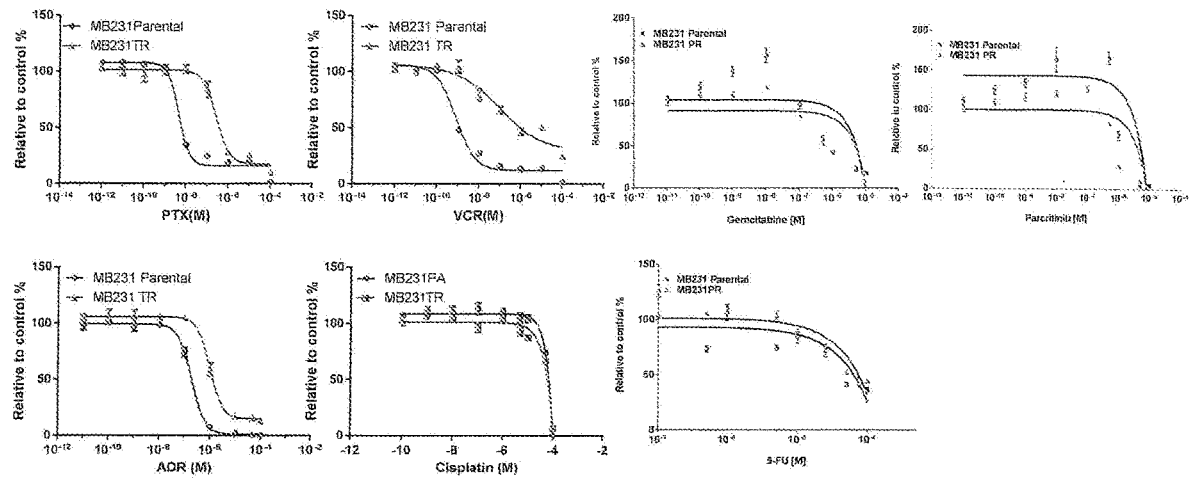
Figure 17:
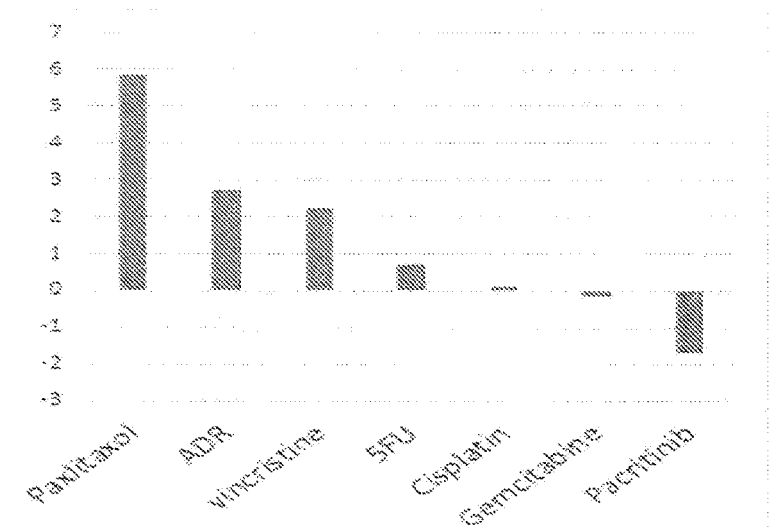

FIG. 17. (a). $IC_{50}$ curves showing cell viability after treatment with paclitaxel (PTX), vincristine (VCR), gemcitabine, doxorubicin (ADR), cisplatin, 5-fluorouracil (5-FU) and pacritinib in parental and pacitaxel-treated MDA-MB-231 (MDA231-PR) cells. (b). Graphical representation of relative sensitivities. (c). Tabulated results of $IC_{50}$ (M), showing marked right shift of the $IC_{50}$ curve with PTX, ADR and VCR, indicating resistance.

Figure 18:
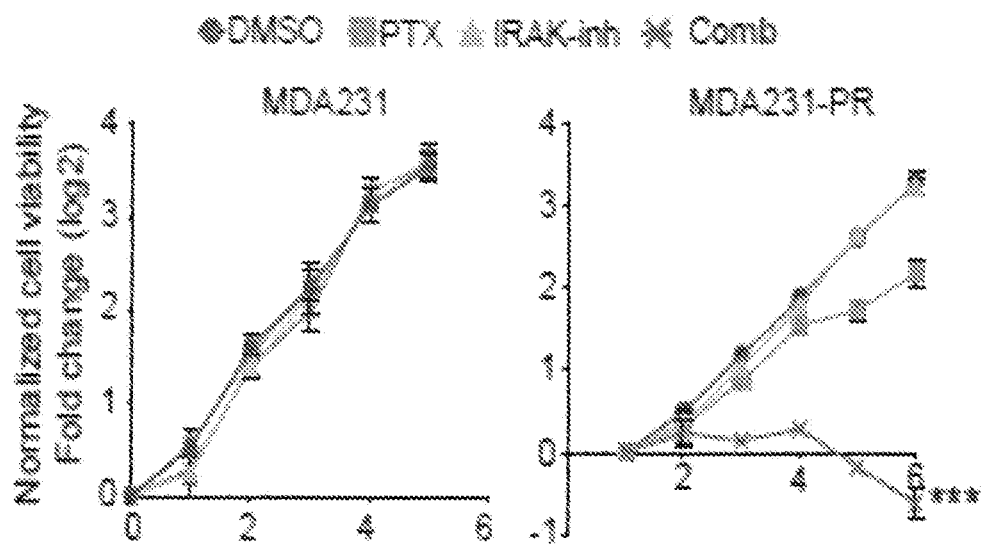

FIG. 18. Cell viability of parental and paclitaxel-resistant MDA231 cells treated with PTX and IRAK-inh (5 µM) alone and in combination.

EXAMPLE 1

IRAK1 is an active kinase of the IL-1/TLR signaling pathway involved in the inflammatory response and aberrant signaling has been implicated in cancers. Here, we show the implication of IRAK1 in breast cancer metastasis and recurrence. IRAK1 was more highly expressed in TNBC compared to luminal lines (P<0.01) and over-expression correlated with shorter overall survival (basal-like BL1, BL2, and mesenchymal-like M, MSL subtypes were evaluated). IRAK1 inhibition reduced proliferation, 3D matrigel growth and mammosphere formation. Conversely, IRAK1 up-regulation in the more aggressive subline MDA231-LM2 potentiated lung metastasis and reduced survival in mouse models.

Of particular interest was our observation that IRAK1 signaling was involved in paclitaxel resistance. Inhibition of IRAK1 inhibited the p38-MCL-1 pathway and down-regulated the anti-apoptotic protein MCL-1, producing massive apoptosis in p-IRAK1-overexpressing MD231 cells resistant to paclitaxel. IRAK1 activation appeared specific to paclitaxel and did not occur with other alternate non-cross resistant agents. IRAK1 also activated NF-κB-induced cytokine production, which in turn enriched the ALDH-positive cell population and enhanced mammosphere formation. These were attenuated with IRAK1 inhibition. Furthermore, we also observed the active phosphorylated form of IRAK1, p-IRAK1, to be upregulated in 6 of 7 tumours that recurred after paclitaxel treatment (P<0.01).

Cells overexpressing p-IRAK1, while no longer responsive to increasing doses of paclitaxel (demonstrating resistance), remained susceptible to cisplatin, gemcitabine and pacritinib. We thus hypothesise that p-IRAK1 can identify paclitaxel-resistant TNBC that will benefit from further treatment with these agents. Cisplatin and gemcatibine are not currently first-line. Preclinical data supports the use of platins in TNBC, but clinicians are cautious of the significant toxicity, as seen with the GeparSixto study (*The Lancet Oncology* 2014:15(7): 747-756). Limiting cisplatin use to p-IRAK1-overexpressing TNBC, where a good response is expected, may justify the toxicity. Gemcitabine is often used after failure of taxanes in metastatic cancer. Conceptually, the use of alternate non-cross resistant agents when response to first-line agents is suboptimal is similar to the Phase III EA1131 trial, and is a more targeted approach compared to the Japanese CREATE-X study. But whereas genetic profiling is required for stratification in the Phase III EA1131, p-IRAK1 is detectable with IHC.

Materials and Methods
Survival Analysis and Molecular Subtype Association Analysis Cancer subtype-specific IRAK1 gene expression analyses based on the gene expression of IRAK1-4 were performed on data generated by the TCGA Research Network: http://cancergenome.nih.gov/. Kaplan-Meier survival analysis was used for the analysis of clinical outcomes. Meta analysis of patients' Relapse Free Survival (RFS), Overall Survival (OS) and Distant Metastasis Free Survival (DMFS) on a total of 10 breast cancer cohorts (Chin breast (Genomic and transcriptional aberrations linked to breast cancer pathophysiologies. *Cancer Cell* 10:529-541.), GSE11121, GSE12093, GSE1456, GSE2034, GSE2603, GSE3494, GSE5327, GSE6532 and GSE7390) comprising 1789 patients were performed using the intrinsic settings of the GOBO algorithm after normalization cross cohorts and platforms (http://co.bmc.lu.se/gobo/) (gene expression-based outcome for breast cancer online. *PLoS One* 6:e17911). Patients were then stratified into two groups based on low (0-50%) and high (50-100%) IRAK1 gene expression. The IRAK1 gene expression analysis on VandeVijver Breast Cohort (A gene-expression signature as a predictor of survival in breast cancer. *N Engl J Med* 347:1999-2009) and Schmidt Breast Cohort (GSE11121) (The humoral immune system has a key prognostic impact in node-negative breast cancer. *Cancer Res* 68:5405-5413) analysis was performed on Oncomine data sets after patient stratification based the metastasis events according to author's original documentations.

Cell Lines, and Reagents

All cell lines were obtained from ATCC (Manassas, Va.) except for MDA231-LM2 (a kind gift from Dr. Yibin Kang, Princeton University) (5). MDA231, BT549, MCF7, T47D, BT474, MB361, MB415, MB436, HS578T and MB157 breast cancer cell lines were grown in Dulbecco's modified Eagle's medium (DMEM) supplemented with 10% fetal bovine serum (FBS). SKBR3 cells were maintained in McCoy's 5A medium. Doxycycline was purchased from Clontech. HCC1806 and HCC1937 were maintained in RPMI medium supplemented with 10% FBS. HMEC and MCF10A normal breast epithelial cell line were purchased from ATCC (Manassas, Va.) and were grown in DMEM/F12 supplemented with 5% horse serum, 20 ng/ml EGF, 0.5 mg/ml hydrocortisone, 100 ng/ml cholera toxin, 10 µg/ml insulin, and penicillin/streptomycin (Invitrogen). All media were supplemented with 5000 U/mL penicillin/streptomycin (Invitrogen). All cells were maintained at 37° C. with 5% $CO_2$. Cells were treated at a final concentration of 0.51 µg/mL for 48-72 hr to induce knockdown of IRAK1.

To establish the Paclitaxel acquired resistant TNBC cell lines, both SUM159PT and MDA231 cells were used. SUM159PT has an intrinsic EC50 of 3.88 nM to Paclitaxel and the treatment was started at a concentration of 5 nM. Once the cells had recovered from the treatment and showed a normal growth rate again, the concentration was increased by 2-folds. During these treatment cycles, only cells with a high intrinsic resistance or those which had acquired resistance to the drug survived. The cycle was further repeated until the stable resistant cell line (SUM159PR or MDA231PR) SUM159PR cells were stably maintained in 1 µM Paclitaxel and MDA231 in 75 nM of Paclitaxel with complete medium, making them at least ~1000-fold more resistant than their parental cell lines.

Recombinant IL-1β, IL-6, IL-8 and CXCL1 were purchased from Peprotech (Rocky Hill, N.J.). Paclitaxel (Cat no: T7402), Vincristine (Cat no: V8879), Doxorubicin (Cat no: D1515) and IRAK inhibitor (Cat no: I 5409) were purchased from Sigma-Aldrich (St Louis, Mo.). SCIO 469 (p38 inhibitor, Cat no: 1671), PS1145 (IKK inhibitor, Cat no: 1568), BAY-11-7082 (IKK inhibitor and anti-inflammatory, Cat no: 2132) and AEG 3482 (JNK inhibitor, Cat no: 1291) were purchased from Axon Medchem (Reston, Va.). Compound K, a metabolite of Ginsenoside Rb1, was purchased from Chengdu Must Bio-Technology Co. (Chengdu, China).

Immunohistochemistry (IHC)

Many reported biomarkers require gene assays for detection. Although IHC on formalin-fixed paraffin embedded tissues is more common in clinical practice, many researchers prefer gene assays because these are quantitative and less prone to variability in results arising from issues with standardisation and interpretation. However, gene assays require specialised equipment and training and are not affordable for many. This is best illustrated by the low uptake of Oncotype DX assay among our patients. Even though Oncotype DX will allow some women to avoid chemotherapy, only 20% of our patients opt for it. Most simply cannot afford the assay; for comparison, Oncotype DX costs SGD 5,000, HER2neu FISH costs SGD 300 and ER/PR/HER2 staining costs SGD 100. Biomarkers detected by IHC (ER/PR/HER2) are still the most affordable and cost effective. Automated immunostainers have reduced much of the variability from technical factors. Strict adherence to protocols and quality control can reduce the variability from suboptimal fixation, inadequate antigen retrieval, different antibody clones, different antibody dilutions, and different scoring systems. Results from IHC are reproducible and reliable enough for therapeutic decisions to be based on.

In the present invention, breast cancer tissue microarray slides BR1505 and IMH-364 were purchased from USA Biomax (Rockville, Md.) and Novus Biologicals (Littleton, Colo.), respectively. Total IRAK1 expression was probed with IRAK1 antibody (clone H-273) purchased from Santa Cruz Biotechnology (Dallas, Tex., cat: sc7883).

IRAK1 Knockdown and Overexpression Constructs

Two different sequences (V3LHS_635467 and V3LHS_635469) from the GIPZ lentiviral shRNA system (Thermo Scientific, MA) were utilized to knock down IRAK1 constitutively in various TNBC cell lines. For inducible knockdown of IRAK1, a shRNA (V2THS-132369) from the TRIPZ doxycycline (DOX)-inducible lentiviral shRNA system that targets the 3-UTR region of IRAK1 was used as described (a gift from Dr Daniel T. Starczynowski, University of Cincinnati). Both constitutive and inducible shIRAK1 stable cells were maintained in complete medium supplemented with Puromycin (1 µg/mL) to select for positive clones. Doxycycline (Clontech, Calif.) was used at a final concentration of 0.5 µg/mL for 48-72 hr to induce knockdown of IRAK1. The specific targeting sequences of shRNAs used to knock down IRAK1 are as summarized in the following table.

| VECTOR | PLASMID ID | Type of KD | CLONE ID | TARGET | TARGET SEQENCE (5'-3') |
|---|---|---|---|---|---|
| pGIPZ | sh1 | Constitutive | V3LHS_635467 | IRAK1's ORF | AATTCATCACTTTCTTCGG |
| | sh2 | Constitutive | V3LHS_635469 | IRAK1's ORF | CCATCACTTTGTAGAAGCG |
| | shIRAK1 for IRAK1 OE rescue | Constitutive | V3LHS_645859 | IRAK1's UTR | ACATGAAACCTGACTTGCT |
| pTRIPZ | shIRAK1 | Inducible | V2THS_132369 | IRAK1's UTR | ATTACTCAAGGACAACCTG |

To generate the IRAK1 over-expressing plasmid (IRAK1 OE), c-DNAs of IRAK1 (transcript 1, accession no: NM_001569.3) was amplified from normal breast tissue controls by PCR and inserted into the GFP based expression vector pBabeMNires (PMN vector, a gift from LZ Penn, University of Toronto, Canada). QuikChange Multi Site-Directed Mutagenesis Kits (Agilent) using the primers computed by manufacture's recommended tool QuikChange Primer Design incorporating desired mutation, was used to alter the residue K239 to Serine (K239S) to render the kinase activity of IRAK1 inactive.

Quantitative-Polymerase Chain Reaction (qPCR)

Total RNA was isolated by using Qiazol (Life technologies, Carlsbad, Calif.) and purified with the RNeasy Mini Kit (Qiagen, Valencia, Calif.). Reverse transcription and quantitative PCR assays were performed using High Capacity cDNA Archive kit and KAPA SyBr Fast qPCR kit (KAPA Biosystems, Wilmington, Mass.). For quantification of mRNA levels, 18S level was used as an internal control. All reactions were analyzed in an Applied Biosystems PRISM 7500 Fast Real-Time PCR system in 96-well plate format. Real-time primer sequences are listed as follows:

(S376) antibody from Genetex (Irvine, Calif., Cat no.: GTX50994). MCL-1 antibody was purchased from Santa Cruz Biotechnology (Santa Cruz, Calif., Cat no.: sc-819). Actin was purchased from Sigma-Aldrich (St Louis, Mo., Cat no.: A5441). Detection of bands was performed with the ChemiDoc™ MP Imaging Systems (Bio-Rad, Hercules, Calif.) and bands were subjected to further densitometric analysis with Image Lab software (Version 4.1, Bio-rad, Hercules, Calif.).

Co-Immunoprecipitation (Co-IP)

Co-IP was performed as described previously (9). The whole cell lysate were extracted with the NE-PER kit (Pierce Biotechnology) and subjected to immunoprecipitation using 2 µg total-IRAK1 antibody (Santa Cruz Biotech, Santa Cruz, Calif., Cat no.: sc-7883). The precipitated protein complex was captured using protein A-Agarose beads (Roche) and extensively washed with the washing buffer (50 mM Tris-HCl, 150 mM NaCl, 0.1% triton). The precipitated proteins were dissolved in SDS sample buffer along with 3 mM DTT, and subjected to immunoblotting analysis. Phospho-IRAK1 (T209) (Assay Biotechnology, Sunnyvale, Calif., Cat no.: A1074) was used for detection.

ELISA Assay and Cytokine Antibody Array

IL-6, IL-8 and CXCL1 levels were assessed using ELISA assay kit (Boster Bio, Pleasanton, Calif.). Supernates of the

| Gene | Forward Primer 5'→ 3' | Reverse Primer 5'→ 3' |
|---|---|---|
| 18S | CGAACGTCTGCCCTATCAACTT | ACCCGTGGTCACCATGGTA |
| IRAK1 | TCAGCTTTGGGGTGGTAGTG | TAGATCTGCATGGCGATGGG |
| IRAK2 | TCTCACCCCCAAACTTG | CTCCCTCGGCCAACACTATTCCA |
| IRAK3 | GCCTGGCAGAGAGACTTTCA | AGGACTCAACACTGCTCCATAG |
| IRAK4 | AGCTTGCAGCAATGGTTGAC | TGTGCCAAGAAAGTGGTGGA |
| IL-1β | GCCAATCTTCATTGCTCAAGTGT | GGTCGGAGATTCGTAGCTGG |
| IL-6 | AGTTCCTGCAGAAAAAGGCAAAG | AAAGCTGCGCAGAATGAGAT |
| IL-8 | ACCGGAAGGAACCATCTCAC | GGCAAAACTGCACCTTCACAC |
| CXCL1 | CCAGCTCTTCCGCTCCTC | CACGGACGCTCCTGCTG |

Western Blotting and Antibodies

Western Blotting was performed as described previously (8). IRAK1 (Cat no: #4359), IRAK4 (Cat no.: 4363), cleaved PARP (Cat no.: #9541), p38 MAPK (Cat no.: #9212), phospho-p38 MAPK (T180/Y182) (Cat no.: #9211), phospho-NF-KappaB p65 (S536) (Cat no. #3031) were purchased from Cell Signaling (Danvers, Mass.). Phospho-IRAK1 (T209) antibody was purchased from Assay Biotech (Sunnyvale, Calif., Cat no.: A1074) and phospho-IRAK1 mammosphere formation assay were collected after 10 days in culture. 1:50 dilution was performed on the supernates before quantifying the amount of cytokines according to the manufacturer's protocol. For cytokine antibody array, supernates collected from the NS or shIRAK1 MB436 mammospheres after 10 days in culture were used directly without further dilution. Semi-quantitative detection of 120 human cytokines and chemokines in the supernates were performed using the RayBio® C-series Human Cytokine Antibody Array C1000 (RayBiotech, Inc., Norcross, GS, Cat no.: #AAH-CYT-1000-2) as per manufacturer's instructions. Detection of dots was performed with the ChemiDoc™ MP Imaging Systems (Bio-Rad, Hercules, Calif.) and the intensity of dots were quantified by densitometric analysis using the ImageJ software. The raw numerical densitometry data is extracted and subjected to background subtraction before normalizing the signal for each cytokines against the Positive Control signals in each cytokine array.

Cell Proliferation Assay and Flow Cytometry (Propidium Iodide Staining)

For cell proliferation assay, the optimal cell seeding was first determined empirically for all cell lines by examining the growth of a wide range of seeding densities in a 96-well format to identify conditions that permitted proliferation for 7 days. Cells were then plated at the optimal seeding density 24 h before siRNA or drug treatment in triplicate. Plates were incubated for 7 days at 37° C. in 5% $CO_2$. Cells were then lysed with CellTiter-Glo (CTG) (Promega, Madison, Wis.) and chemiluminescent signal was detected with a microplate reader on Day 0, 1, 3, 5 and 7. In addition, an untreated plate of cells was harvested at the time of drug or siRNA addition ($T_0$) to quantify the starting number of cells. CTG values obtained after the 7 day treatment were expressed as percentages of the $T_0$ value and plotted against time of treatment.

Cell cycle analysis was done by DNA content quantification to quantify the sub-G1 population which is reflective of the extent of cell death. Briefly, the cells were fixed with 70% ethanol and stained with propidium iodide (50 μg/ml) staining. The stained cells were analyzed by FACScalibur (BD Bioscience) and quantified by using CellQuest software (BD bioscience).

3D Matrigel Assay 8-well chamber slides (Falcon, cat: 354656, Falcon) were precoated with 7.6 mg/mL growth factor-reduced Matrigel (Falcon, cat: 354230, Falcon) for 30 min at 37° C. Approximately $5 \times 10^3$ for MDA231, $1 \times 10^4$ for MB436 and MB468, $1.5 \times 10^4$ cells for BT549 with indicated treatments were seeded in each well with DMEM containing 10% (vol/vol) FBS and 150 μg/mL Matrigel. Medium were replenished every 3 days and cell growth was monitored every 3 days by imaging over duration of 10-14 days.

Mammosphere Formation Assay

Active growing cells were treated with 0.05% trypsin for 10 minutes then passed through 0.4 μm cell strainer to achieve single cell suspension. Cells were plated (MDA231: $1 \times 10^4$; MB436: $3 \times 10^4$; MB468: $4 \times 10^4$ cells/well, BT549: $3 \times 10^4$, MDA231-LM2: $3 \times 10^4$) seeded in 6-well ultra-low attachment plates (Corning, Corning, N.Y., cat: CLS3471) in Mammocult medium (Stem cell Technologies, Vancouver, BC, Canada), supplemented with fresh hydrocortisone (0.51 μg/ml) and heparin (1:500). Tumorspheres were cultured for 7 days prior to being counted and photographed. Imaging and quantification were done using GelCount™ apparatus and associated software (Oxford Optronix, Abingdon, UK). For serial passages of tumorsphere formation assay, the spheres were collected by gentle centrifugation, dissociated to single cells for passaging tumorspheres every 14 days and counted. Tumorspheres were photographed and quantified 7-12 days later using a GelCount Colony Counter after staining with INT.

Anchorage-Independent Colony Formation Assay

Experiments were carried out in 6 well plates coated with a base layer of DMEM containing 0.6% agar, cells were seeded at a density of 10,000 cells per well in DMEM containing 0.3% agar, 10% fetal bovine serum for 14 days. Colonies were stained with iodonitrotetrazolium chloride (INT, Sigma, St. Louis, Mo.) overnight. The number and size of colonies were analyzed using GelCount (Oxford Optronix) according to the manufacturer's instruction.

Transwell Invasion Assay

Transwell invasion assay were performed using 24-well FluoroBlok transwell insert (Falcon, Dallas, Tex.) with a pore size of 8 μm according to manufacturer suggested protocol. In brief the inserts were pre-coated with growth factor-reduced Matrigel (BD Biosciences, cat: 354230 Falcon) for 6 hrs at 37° C. at the concentration of 600 μg/ml. Then $5 \times 10^4$ of cells were seeded into each insert in DMEM containing 0.25% FBS as serum starvation medium. DMEM supplemented with 0.5% FBS and 100 ng/ml EGF was added outside the chamber as chemo-attractant. Invaded cells were fixed after 48 hours of incubation by using 3.7% formaldehyde and stained with 25 ug/ml propidium iodide (Sigma-Alrich). 10 fields per inserts were scanned and numbers of invaded cells were counted with Cellomics ArrayScan.

ALDEFLUOR Assay

ALLEFLUOR assay was performed using the manufacturer's recommended protocol (ALDEFLUOR kit, Stemcell Technologies; catalogue number: #01700). In brief, one million single-cell suspensions were centrifuged and resuspended in ALDEFLUOR assay buffer supplied in the kit. Each sample cells were incubated with or without an ALDH-specific inhibitor 15 mM diethylaminobenzaldehyde in the presence of 0.15 mM ALDH substrate. ALDEFLUOR stainings were detected using fluorescein isothiocyanate channel of a FACSCalibur Flow Cytometry System (BD Biosciences) after 25 min incubation at 37° C. Diethylaminobenzaldehyde inhibitor control sample was used as sorting gate reflecting background fluorescence levels for each cell lines.

Dual Luciferase Reporter Assay

NF-κB-specific reporter plasmid pGL4.32 and its negative control pGL4.15 were purchased from Promega (Madison, Wis.). Cells were harvested 48 hr after transfection and analyzed with the Dual Luciferase system (Promega, Madison, Wis.) according to the manufacturer's protocol. To analyze luciferase activity, Firefly signals of pGL4.32/pGL.15 were normalized to Renilla signals of pRL-null in respective samples. pGL4.32/pRL-null ratio were further normalized to pGL4.15/pRL-null ratio to obtain normalized values corrected for the changes of basic transcription activity for indicated treatment of the cells.

Animal Studies

For the subcutaneous xenograft model, $7.5 \times 10^6$ MB436 cells and $5 \times 10^6$ MDA231 carrying doxycycline inducible shIRAK1 (n=12 for each cell line) were mixed with Matrigel (BD Biosciences, Singapore, cat: 354234) at 1:1 ratio in a 50 μl total volume. Doxycycline (100 mg/kg, B.D) (Clonetech, Mountain View, Calif.) was administered via oral gavage to induce IRAK1 knockdown in the shIRAK1 group (n=6) while control group were given PBS (n=6). Tumors were measured by vernier caliper weekly and the tumor volume was calculated with the following formula: $V = W \times W \times L / 2$.

For the orthotropic mammary fat pad model, $1 \times 10^6$ MDA231-LM2 cells carrying PMN vector, shIRAK1 and IRAK1 rescue (n=8 each group) were mixed with Matrigel (BD Biosciences, Singapore, Cat no.: 354234) at 1:1 ratio in a 20 μl total volume. Cells were engrafted in mammary fat of 6-8 weeks old female NOD-SCID mice on Day 0. IRAK-inh (4 mg/kg, n=6) was administered daily from Day 20 to Day 37 via intraperitoneal (I.P) injection. Primary mammary tumors were measured by vernier calliper weekly and the tumor volume was calculated with the following formula: V=W×W×L/2 before surgically harvesting the primary tumors on Day 27. Harvested tumors were measured by mass and dimensions. Lung metastasis development was monitored weekly by Bioluminescence Imaging. For ex-vivo imaging of whole lung, mice were first sacrificed via carbon dioxide inhalation and lungs were harvested immediately. The lungs were submerged individually in 150 µg/ml of Promega VivoGlo™ Luciferin (Madison, Wis.) in PBS for 5 mins before imaging with IVIS imaging System (Xenogen, Alameda, Calif.).

For the tail vein xenograft model, $1 \times 10^5$ MDA231-LM2 cells carrying PMN vector and IRAK over-expression (n=10 each group) were injected via lateral tail vein in 6-8 weeks old female NOD-SCID mice. Lung metastasis development was monitored weekly by Bioluminescence Imaging.

For bioluminescence imaging, 150 mg/kg of Promega VivoGlo™ Luciferin in PBS were given to mice intraperitoneally (I.P) and imaged with IVIS imaging System (Xenogen, Alameda, Calif.) until 6 week post injection. The photon values were recorded using Living Image 3.1. Differences among groups and treatments were determined by ANOVA followed by Student's t test (***p<0.001; n.s., not significant). Error bars represent means±SEM. Animal survival curve was generated using Kaplan-Meier analysis and the statistical parameters were calculated by Log-Rank (Mantel-Cox) test using Graphpad Prism software (Version 6.0) as described previously in *Proc Natl Acad Sci USA* 110:11121-11126.

Patient derived xenograft (PDX) mouse models may also be generated with fresh tumours obtained from patients newly diagnosed with TNBC. We aim to have treatment naïve tumours collected from surgery and biopsy, and also post-neoadjuvant chemotherapy treated tumours. In an embodiment, 10 successful TNBC PDX models may be generated and plan for 200 NSG mice (assuming a 30% uptake, and taking into account subsequent passages). Fresh tumour tissue collected from core biopsy (2 cores) or surgery (2 5 mm cubes) may be transferred in fresh culture media to the laboratory, washed with phosphate-buffered saline supplemented with Antibiotic-Antimycotic (Invitrogen, cat 15240-062), minced into 2 mm cubes on ice and orthotopically transplanted into the mammary fat pad of 8 to 12-week-old NSG mice (NOD.Cg-Prkdc$^{scid}$ Il2rg$^{tm1Wjl}$/SzJ, Jackson Laboratory West, Sacramento, Calif., USA) under sterile conditions. Successful xenografts will typically emerge 3 to 6 months later. Established xenografts are passaged from mouse to mouse to expand the numbers. A portion of the xenograft are stored as fresh frozen material for characterisation, and a portion will be fixed and processed for histological correlation with the original tumour.

Immunohistochemical Staining (IHC) for Xenograft Tumors

Harvested tissues were fixed in 10% Formalin solution, (HT501128, Sigma-Alrich). Tissues were dehydrated and embedded in paraffin. Paraffin-embedded tissue sections (5 µm thick) were cut, deparaffinized, and rehydrated, and antigens were retrieved using pH 6 Sodium Citrate. The sections were then incubated in 0.06% Hydrogen Peroxide at room temperature to block endogenous peroxidase. The slides were incubated overnight with anti-IRAK1 (Cat no.: sc-7883), anti-vimentin (Cat no.: sc-6260) from Santa Cruz Biotech (Santa Cruz, Calif.), and anti-IL6 from Abcam (Cambridge, Mass., Cat no.: ab1543670) overnight, followed by 60 min incubation with Anti-Mouse IgG/Rabbit IgG (Cat. No. PK-6200) and 60 min of Avidin DH and Biotinylated Horseradish Peroxidase H. ImmPACT™ DAB Peroxidase Substrate (Cat. No. SK-4105) was used as the chromogen. Vector® Hematoxylin QS (H-3404) was used as counter-stain.

Immunohistochemical Staining (IHC) for TMA and Clinical Samples

Breast Cancer Tissue microarray slides BR1505 and IMH-364 were purchased from US Biomax (Rockville, Md.) and Novus Biologicals (Littleton, Colo.) respectively. Paraffin embedded sections of primary and recurrent tumor were obtained from Tan Tock Seng Hospital, Singapore and John Wayne Cancer Institute (CA, USA). Staining and image analysis of tissue microarray and the clinical samples were performed by Histopathology Department from Institute of Molecular and Cell Biology, Agency for Science, Technology, and Research (A*STAR), Singapore. Briefly, paraffin-embedded tissue sections and the TMAs were deparaffinized, rehydrated, antigens were retrieved by Proteinase K solution; sections were then incubated in 3% H2O2 at room temperature to block endogenous peroxidase. Slides were incubated in total-IRAK1 antibody from Santa Cruz Biotech (Santa Cruz, Calif., Cat no. sc-7883) or phospho-IRAK1 (S376) antibody from Genetex (Irvine, Calif., Cat no.: GTX50994) for 45 mins after diluting both antibodies at 1:100, followed by 30 min incubation with anti-mouse Labelled Polymer (Dako, Calif.).

Specificity of the immunostaining was determined by the inclusion of isotype-specific IgG as negative control. The detection system was DAB+ Substrate-Chromogen Solution (Dako, Calif.). The sections were counterstained with hematoxylin. Slides were scanned at 20× using a Leica SCN400 slide scanner (Leica Microsystems, Germany). Images were exported to Slidepath Digital Image Hub (Leica Microsystems, Germany) for viewing. Tissue micro-array cores were analyzed using the Measure Stained Cells algorithm of Slidepath Tissue IA software (Leica Microsystems, Germany). The total cellular H-score were then further normalized and expressed as Z-score after conversion with the following formula, z=(Total cellular H-score of each tumor–mean H-score)/SD of all tumors. Data was collated using Microsoft Excel. Scanning and image analysis was performed by the Advanced Molecular Pathology Laboratory, IMCB, Singapore.

Statistical Analyses

All in vitro experiments were repeated at least three times unless stated otherwise, and data are reported as mean+SEM. To normalize the expression of each patient cohorts, expression values were normalized by calculating the z-score for each independent dataset, the differences were assessed by two-tailed students' using Student's t test or one-way ANOVA for multiple group comparisons using GraphPad Prism 6 software. Animal study survival curves were plotted using Kaplan-Meier analysis and the statistical parameters were calculated by Log-Rank (mantel-Cox) test using Graphpad Prism. In all statistical tests the resulting p≤0.05 was considered significant unless stated otherwise.

Results

Preliminary Studies

We performed a retrospective review of 159 consecutive patients with non-metastatic disease who received neoadjuvant chemotherapy from 1$^{st}$ Jan. 2006 to 31$^{st}$ Dec. 2013. Majority of patients (84%) had residual invasive disease (pCR was lower than reported in literature because many patients had Stage III disease). Response was higher among ER-negative tumours (14% vs 5%). Survival correlated with pathological response (FIG. 14).

TABLE 1

Details of 159 patients receiving neoadjuvant chemotherapy.

|  | Number of patients | Recurrence | Death |
| --- | --- | --- | --- |
| Disease stage | | | |
| Stage II | 41 | 6 | 3 |
| Stage III | 118 | 28 | 21 |
| Pathological response* | | | |
| No residual disease | 11 | 0 | 0 |
| Residual DCIS | 12 | 3 | 1 |
| Residual invasive tumour | 118 | 38 | 18 |

*among 141 patients who underwent subsequent surgery (16 refused surgery, 2 foreigners returned home for surgery)

We evaluated 8 patients with ER-negative tumours who received neoadjuvant chemotherapy (with regimen including paclitaxel) and later developed recurrent disease. In 6 cases, p-IRAK1 staining was more intense in the residual tumour post-chemotherapy (P=0.04) (FIGS. 15A and B) and this correlated with shorter median time to recurrence (15.6 mth vs 29.0 mth) and reduced overall survival (45.5 mth vs 65.9 mth). Higher p-IRAK1 levels were also observed in the recurrent tumour compared to the original tumour (FIG. 2B). On the other hand, p-IRAK1 levels tended to decrease post-chemotherapy in those without recurrence (FIG. 15C). Taken together, these support our hypothesis that p-IRAK1 induction correlates with paclitaxel resistance and predicts for recurrence.

[Are these 8 Patients Part of the 159-Patient Study?]

A marked induction of p-IRAK1 was observed in parental MDA-MB-231 cells, which expressed low levels of IRAK1, after exposure to paclitaxel over 48 hours (FIG. 16A). This was not seen with the non-cross resistant agents doxorubicin (ADR) and cisplatin (FIG. 16B), thereby suggesting that IRAK1 activation was specific to acquired paclitaxel resistance. Cytokines IL1B, IL6 and IL8 were induced following treatment with paclitaxel treatment, resulting in expansion of the ALDH-positive cell population and potentiated mammosphere formation. These effects were markedly impaired upon IRAK1 knockdown, demonstrating the role of IRAK1 in acquired paclitaxel resistance.

Next, we compared sensitivities of parental and paclitaxel-treated MDA231 cells (presumably paclitaxel resistant) to common agents in breast cancer regimens and the IRAK1 inhibitor pacritinib. Paclitaxel-treated MDA231 cells, over-expressing p-IRAK1, were markedly resistant to paclitaxel, and to a lesser extent, doxorubicin and vincristine as well (FIG. 17). Paclitaxel-resistant cells will then be exposed to: 1) paclitaxel, 2) cisplatin, 3) gemcitabine, and 4) paclitaxel and pacritinib (at doses optimised above). Induction of p-IRAK1 and cell viability will be compared between the agents (as described above), to determine whether the response to any one agent can be stratified by TNBC subtype or p-IRAK1 levels. This will be important in allowing clinicians to select the most appropriate agent in a given clinical scenario. Paclitaxel-resistant cells were sensitive to cisplatin, gemcitabine and pacritinib. Interestingly, response to 5-fluorouracil was poor in both parental and paclitaxel-resistant cells.

The IRAK1 inhibitor, IRAK-inh, on its own had no effect on paclitaxel-resistant MDA231 cells, yet produced dramatic cell death in combination with paclitaxel (FIG. 18). We showed that this was primarily mediated through inhibition of p38-MCL-1 signaling. NF-κB-induced IL-6, IL-8 and CXCL1 cytokine production was also affected but did not directly induce apoptosis. The synergistic effect of IRAK-inh and paclitaxel suggests a potential for IRAK1 inhibition to overcome paclitaxel resistance.

IRAK1, but not Other IRAK Genes, is Overexpressed in a Subset of Breast Cancers and is Indicative of Poor Prognosis In search of the upstream molecular regulators of NF-κB-related inflammatory gene network that might be aberrantly expressed in breast cancers, we interrogated The Cancer Genome Altas (TCGA) database and identified the upregulation of Interleukin 1 receptor associated kinase 1 (IRAK1) in various subtypes of breast tumors in comparison to the normal breast epithelial tissues (FIG. 1A, p<0.0001, Tukey's multiple comparisons test). The other three IRAK family members, however, did not show such a change (FIG. 1A). Of notice, IRAK1 expression is particular higher in the basal breast tumors as compared to other subtypes of breast tumors (FIG. 1A, p<0.0001, Tukey's multiple comparisons test).

Immunohistochemistry (IHC) analyses of two tissue microarrays (TMAs) (BR1505 and IMH364) composed of two independent sets of breast invasive ductal carcinoma specimens with various molecular subtypes confirmed the upregulation of IRAK1 protein expression in all the breast cancer subtypes particularly in TNBC compared to the normal tissues (FIG. 1B).

To explore a role of IRAK1 in clinical outcomes, we performed meta-analyses using GOBO database to study relationship between IRAK1 expression and disease progression and patient survival. The results revealed that high IRAK1 expression correlated with reduced relapse free survival, overall survival and distant metastasis free survival ($p=2.1 \times 10^6$, $p=0.0047$, $p=0.017$ respectively, FIG. 1C), suggesting a prognostic value of IRAK1 in breast cancer. Taken together, these findings suggest a potential role of IRAK1 deregulation in breast cancer, particularly in TNBC. These findings do suggest a potential role of IRAK1 in breast tumorigenesis in any case.

Genetic and Pharmacologic Inactivation of IRAK1 Effectively Abrogate Aggressive Growth of IRAK1-High Expressing TNBC Cells To examine whether the above finding in breast cancer clinical samples can be similarly found in breast cancer cell lines in vitro, we analyzed a panel of 14 breast cancer cell lines of luminal and basal origins, as well as two non-cancerous breast epithelial cell lines MCF10A and HMEC. RT-PCR analysis shows that IRAK1 mRNA is upregulated in 80% of breast cancer cell lines as compared to MCF10A and HMEC, in which IRAK1 expression is obviously more enriched in basal lines compared to luminal lines (FIG. 2A). For comparison, IRAK4, the other IRAK family member with the kinase activity, did not show a consistent change between luminal and basal lines (FIG. 2A). A similar result was also obtained in GOBO database analysis that contains expression data of 55 breast cancer cell lines (www.gobo.com) (FIG. 7A). Western blot analysis confirmed the RT-PCR results and again showed higher levels of IRAK1 protein expression in basal versus luminal, and this was not observed for IRAK4 (FIG. 2B). We further show that the three basal/TNBC lines BT549, MB436 and MB468 with higher levels of IRAK1 also displayed higher levels of phosphorylated IRAK1 (T209) compared to IRAK1-low expressing MDA-MB-231 cells (thereafter called MDA231 cells), indicating that the level of IRAK1 expression is associated with its activity (FIG. 1F).

To study a functional role of IRAK1 in TNBC, we knockdown IRAK1 expression with two independent small hairpin RNA (shRNA) constructs that independently express Green Fluorescence Protein (GFP) in TNBC cell lines that express high or low levels of IRAK1. IRAK1 knockdown in IRAK1-high expressing BT549 and MB436 cells only caused a modest effect on cell proliferation on day 7, but prolonged culture to day 20 led to a gradual depletion of GFP positive cells but this was not seen in IRAK1-low expressing MDA231 cells (FIG. 7B-D). This suggests that IRAK1 has a role in conferring proliferative advantage in TNBC cells, though not robustly seen in monolayer culture.

We next sought to determine the effect of IRAK1 knockdown on aggressive growth phenotypes of TNBC, such as 3D Matrigel growth and mammosphere formation. To facilitate the study, we made use of an doxycycline (DOX)-inducible shRNA system in which adding doxycycline resulted in depletion of IRAK1 (FIG. 2D). Knockdown of IRAK1 resulted in robust inhibitions of both 3D Matrigel growth and mammosphere formation in serum-free suspension culture in IRAK1-high expressing cells (BT549, MB436 and MB-468), but not in MDA231 cells that express a low level of IRAK1 (FIGS. 2E, 2F, and 7E). Moreover, IL-1β-evoked Matrigel cell invasion in MB436 and BT549 cells was also markedly impaired upon IRAK1 knockdown (FIG. 7F). In contrast, MDA231 cells did not respond to IL-1β treatment and thus was insensitive to IRAK1 knockdown (FIG. 7F). These in vitro effects were also seen in vivo as MB436, but not MDA231, xenograft tumors bearing IRAK1 shRNA exhibited much reduced growth in NOD/SCID mice (FIG. 2G). Taken together, our results demonstrated an indispensable role of IRAK1 in both the aggressive growth of TNBC cells in vitro and the tumorigenicity in vivo.

Lastly, we asked whether pharmacologic inhibition of IRAK1 recapitulates the IRAK1 gene knockdown phenotypes. IRAK-inh is a commercially available IRAK1/4 inhibitor which has been recently shown to have potent activity against IRAK1 in Myelodysplastic Syndrome[20]. As expected, IRAK-inh treatment effectively abolished the p-IRAK1 in TNBC cells (FIG. 2H), leading to marked inhibition of 3D Matrigel and mammosphere growth of BT549, MB436 and MB468 cells, but not MDA231 cells (FIG. 2I and FIG. 8A-2B). It had also no effect on non-cancerous MCF10A and HMLE cells (FIG. 8C).

Lack of sensitivity of MDA231 cells to IRAK-inh may indicate a deficiency of IL-1/IRAK1 signaling in these cells. Indeed, treatment with recombinant IL-1β induced a fast induction of p-IRAK1 in IRAK-inh sensitive MB436 cells which was abrogated by IRAK-inh treatment, whereas the same treatment did not elicit a similar response in MDA231 cells (FIG. SD). Taken together, these data suggest that IRAK-inh is active against TNBCs that express high levels of IRAK1 and are proficient in IL-1/IRAK1 signaling.
IRAK1-Directed Activation of NF-KB and Related Cytokine Production is Functionally Required for the Mammosphere Growth of TNBC.

Given that previous studies have shown roles of NF-κB-dependent cytokine production in supporting breast cancer CSC[14,24,25], we reasoned that the reduced mammosphere growth following IRAK1 knockdown might result from reduced cytokine production and thus should be rescued by conditional medium of untreated cells. Indeed, addition of the supernatant of control MB436 sphere cells to the IRAK1-depleted MB436 cells restored the sphere growth capacity, supporting that the IRAK1-regulated cytokine production might be crucial to support the CSC growth of TNBC cells.

To identify the cytokines that are crucial for IRAK1-regulated CSC growth, we used RayBio Human Cytokine Antibody Array and performed quantitative cytokine profiling of conditional sphere growth medium of MB436 cells with and without IRAK1 knockdown. We identified a number of cytokines showing reduced productions upon IRAK1 knockdown.

Among them, IL-6, IL-8 and CXCL1, previously shown to be important for breast cancer CSC[12,13,26], emerged as the top three NF-κB-related cytokines that were most abundantly detected and downregulated after IRAK1 knockdown (FIG. 3B). Consistently, knockdown of IRAK1 caused significant inhibition of NF-κB reporter activity (FIG. 3C).

Enzyme-linked immune-sorbent assay (ELISA) confirmed that IRAK1 knockdown reduced the secretions of IL-6, IL-8 and CXCL1 in the supernatant of MB436 cells which was restored upon addition of conditional medium of mock-treated cells (FIG. 3D). We further show that the individual additions of recombinant IL-6, IL-8 or CXCL1 were unable to restore the sphere growth, while their combination was sufficient to achieve this (FIG. 3E). These findings identify an essential role of IRAK1-regulated cytokine secretion in maintaining the CSC growth.

Of notice, IRAK1 depletion significantly reduced cytokine secretion in BT549 and MB436 but to a much lesser extent in MDA231 (FIG. 3F). We postulated that the remaining levels of cytokines in MDA231 cells after IRAK1 knockdown is still sufficient to promote mammosphere formation. Indeed, the conditioned medium harvested from MDA231 shIRAK1 cells was sufficient to fully rescue the inhibition on the mammosphere formation of MB436 shIRAK1 cells (FIG. 3G). Thus, unlike other TNBC cells with high levels of IRAK1, the NF-B-related cytokine production in MDA231 cells is substantially less dependent on IRAK1, which could account for the lack of sensitivity of MDA231 cells to IRAK1 depletion. Consistent with the above phenotypes, we saw that IRAK-inh treatment resulted in strong reduction in IL-8 and CXCL1 secretion in IRAK-inh-sensitive TNBC cells but to a much lesser extent in IRAK1-inh-resistant MDA231 cells (FIG. 3H).
Breast Cancer Metastasis Exhibits Increased Expression of IRAK1 and Gain of Growth-Dependency on IRAK1 Signaling Given a strong role of IRAK1 in invasive growth and mammosphere formation, we next evaluated the clinical relevance of IRAK1 expression in relation to breast cancer progression. We found that IRAK1 is expressed in much higher levels in poorly differentiated high grade (grade 3) tumors compared to relatively well-differentiated grade 1-2 tumors, as revealed by both Oncomine analysis and immunohistochemistry verification using TMA BR1505 (FIG. 4A). Moreover, IRAK1 expression shows progressive increase from normal adjacent tissues to matched primary and metastasis tissues as shown in 6 out of 9 primary-metastasis pairs in TMA IMH-364 (FIG. 4B), indicating an association of IRAK1 expression with metastasis progression. Consistent with this, Oncomine analysis of two independent breast cancer cohorts shows a positive correlation of IRAK1 expression with metastasis events at 5 years post-surgery (FIG. 9A).

To recapitulate the above clinical observation in vitro, we compared the MDA231 and its derived lung metastatic subline MDA231-LM2[27]. Although the two lines exhibited no apparent difference in monolayer growth, MDA231-LM2 cells compared to MDA231 cells displayed much more aggressive phenotype as shown in 3D Matrigel and mammosphere growth (FIG. 4C). Interestingly, metastatic MDA231-LM2 cells showed increased levels of both total IRAK1 and p-IRAK1, as well as p-p65NF-κB compared with the parental MDA231 cells (FIG. 4D). They also exhibited increased transcription and secretion of IL-6, IL-8 and CXCL1 (FIGS. 9B and 9C). Of notice, ILIA and IL1B, as well as IL1R, which encodes IL-1 receptor, also showed increased expression in MDA231-LM2 cells (FIG. 9B), suggesting an augmented autocrine feedback loop activating IL-1/IRAK1 signaling.

Moreover, compared to parental MDA231 cells that were unresponsive to IL-1β treatment, MDA231-LM2 cells now became responsive to recombinant IL-1β treatment by showing robust p-IRAK1 and cytokine inductions, (FIGS. 4E and 4F). These results indicate a gain of IL-1/IRAK1 signaling activity in metastatic MDA231-LM2 cells.

Accordingly, an IRAK1 shRNA targeting the 3'-UTR of IRAK1 was able to effectively inhibit the 3D Matrigel growth and mammosphere growth of MDA231-LM2 cells (FIG. 9D) and this inhibition was readily rescued by ectopic IRAK1 (FIG. 4G). Consistently, IRAK1-inh phenocopied the effects of IRAK1 knockdown, leading to impaired 3D Matrigel and mammosphere growth in MDA231-LM2 cells only (FIG. 4H). Furthermore, application of cell culture supernatant of mock-treated MDA231-LM2 cells to the culture of IRAK1-inh-treated MDA231-LM2 cells led to a complete rescue of mammosphere growth (FIG. 4I), which echoed the restored levels of cytokines (FIG. 4J).

Of important notice, unlike IRAK1 knockdown that selectively affects MDA231-LM2 cells but not MDA231 cells, RELA knockdown eliminated the aggressive growth of both cell lines (FIGS. 9E and 9F). This indicates that although NF-κB is important for both parental and metastatic MDA231, it has gained preferential dependency on IRAK1 in MDA231-LM2 cells, resulting in selective susceptibility to IRAK1 interference.

Moreover, as both the kinase function and scaffold function have been implicated in IRAK1 signaling in a context-dependent manner[28], we sought to determine whether or not the kinase activity of IRAK1 is required for the aggressive growth of MDA231-LM2 cells. As shown in FIG. 5K, expression of ectopic wild-type IRAK1 in MDA231-LM2 cells had no obvious effect on the monolayer growth but enhanced the aggressive growth phenotypes. In contrast, ectopic expression of a kinase-dead IRAK1 that carries a point mutation in the ATP-binding pocket (K239S) induced strong inhibitory effects on 3D Matrigel and mammosphere growth, though lack of effect on monolayer growth (FIG. 10A). Consistently, wild-type IRAK1 increased the secretions of IL-6, IL-8 and CXCL1, while IRAK1 K239S yielded opposite effects (FIG. 4B). These results confirmed an indispensable role of IRAK1 kinase activity in aggressive phenotypes of TNBC.

Lastly, we asked whether IRAK1 is functionally sufficient to enable aggressive growth. We explored the effects of ecotopic IRAK1 expression on non-cancerous mammary epithelial cells MCF10A and HMLE cells in vitro. Although ecotopic IRAK1 expression in MCF10A cells only had a modest effect on cell proliferation (FIG. 11A), it markedly enhanced soft agar growth (FIG. 11B), indicating its ability for oncogenic transformation. Ectopic IRAK1 also enhanced the 3D Matrigel and mammosphere growth in MCF10A and HMLE cells (FIG. 10L and SLM), and induced the expressions of IL6, IL8 and CXCL1 mRNAs (FIG. 4C). Moreover, expression of ectopic IRAK1 greatly potentiated IL-1β-induced invasion in MCF10A and HMLE cells (FIG. 4N). These findings indicate that IRAK1 is functionally sufficient to enable malignant transformation and aggressive growth of mammalian epithelial cells.

Inhibition of IRAK1 Inhibits Breast Cancer Growth and Metastasis In Vivo

To investigate whether IRAK1 is required for TNBC progression in vivo, we assessed the effects of IRAK1 knockdown on TNBC xenograft mammary fat tumor growth and subsequent lung metastasis progression in NOD/SCID mice. To this end, we made the use of the MDA231-LM2 cells expressing the IRAK1 shRNA that targets the 3'-UTR of IRAK1 to allow functional rescue by ectopic IRAK1. The results show that the primary tumor growth was markedly reduced in mice bearing tumors expressing IRAK1 shRNA, compared to the control, and this knockdown effect was completely rescued in mice bearing tumors expressing both IRAK1 shRNA and ectopic IRAK1 (FIG. 5A). Immunohistochemistry analysis of the harvested tumors indicates reduced expression of IL-8 in IRAK1-depleted tumors compared to control tumors, though cell proliferation marker Ki67 remained unchanged (FIG. 5B).

To assess lung metastasis, mammary fat tumors were removed after 21 days and the lung metastasis was assessed by lung imaging analysis. The effect of IRAK-inh on metastasis was also evaluated by administering the drug 7 days before the tumor removal for 14 days. As shown in FIG. 5C, both IRAK1 knockdown and IRAK1-inh treatment markedly reduced the lung metastasis, and the knockdown effect was rescued by ectopic IRAK1. These findings indicate that IRAK1 is required for TNBC tumor growth and metastatic progression and pharmacologic inhibition of IRAK1 is able to abolish metastatic progression.

To assess the effect of, IRAL1 overexpression on metastasis, intra-venous injection of MDA231-LM2 cells expressing control or ectopic IRAK1 in NOD/SCID mice was used. The result shows that ectopic IRAK1 drove a rapid formation of lung colonization and metastatic nodules as compared to the vector control as determined by both in vivo and ex vivo lung imaging and whole lung staining (FIGS. 5D and 5E). Immunohistochemistry analysis of the affected lungs indicated increased expression of IL-6 in tumors expressing ectopic IRAK1 (FIG. 5F). As a result, mice bearing ectopic IRAK1 suffered accelerated death compared to the control mice (FIG. 5G). Taken together, our results demonstrate through both loss and gain of function studies a crucial role for IRAK1 in driving breast cancer growth and metastasis.

Chemotherapy Treatment Activates IRAK1 Signaling, Leading to Acquired Chemoresistance CSCs are regarded as crucial for relapse after chemotherapy[29]. It has also been becoming evident that chemotherapy is able to induce CSCs repopulation through induction of inflammatory cytokines[30-32]. We next investigated whether IRAK1 signaling participates in chemotherapeutic response and contributes to CSC enrichment. Exposure of SUM159 and MDA231 cells to 5 nM Paclitaxel for 48 hours resulted in marked induction of p-IRAK1 (FIG. 6A and data not shown). It also induced the expressions of IL1B, IL6 and IL8 mRNAs in MDA231 cells, which was markedly impaired upon IRAK1 knockdown (FIG. 6B). This effect was not limited to Paclitaxel as similar findings were also observed in cells treated with Vincristine, that is also used for advanced breast cancer (FIG. 12A).

Consistent with roles of inflammatory cytokines in CSC formation, MDA231 cells pretreated with 10 nM Paclitaxel for 4 days resulted in increased mammosphere forming capacity of the remaining viable cells and this effect was compromised upon IRAK1 knockdown (FIG. 6C). These results indicates IRAK1 signaling participates in chemotherapy response and contributes to chemotherapy-induced CSC enrichment. Consistent with this in vitro observation, IHC analysis of 5 primary and matched chemo-recurrent breast tumor samples showed increased p-IRAK1 expression in recurrent tumors compared to matched primary tumors in three patients, indicating a clinical relevance of p-IRAK1 induction by chemotherapy (FIG. 6D).

Having shown a role of IRAK1 in Paclitaxel response in TNBC, we next sought to determine whether IRAK1 activation contributes to TNBC acquiring resistance to Paclitaxel. To this end, we used MDA231 and SUM159 cell lines (express low levels of IRAK1) and generated Paclitaxel-resistant lines through step-wise exposing to increasing concentrations of Paclitaxel over three months (FIG. 12B). As anticipated, both of the resulting Paclitaxel-resistance cell lines (PR) displayed increased p-IRAK1 and p-p65 NF-κB (FIG. 6E), indicating gain of activity of IRAK1-NF-κB signaling in TNBC cells upon acquisition of resistance to Paclitaxel. Intriguingly, IRAK-inh, when combined with respective sub-toxic concentrations of Paclitaxel induced dramatic loss of cell viability in both Paclitaxel-resistant cell lines but not in the parental cells (FIG. 6F), which was accompanied by massive apoptosis (FIG. 12C). The Paclitaxel resistant cells also show resistant to Vincristine treatment and combination of IRAK-inh with Vincristine also had a similar effect on apoptosis induction (FIG. 12D). These results indicate that the therapeutic targeting of IRAK1 is able to circumvent the chemoresistance by inducing massive apoptosis.

We next investigated the molecular basis on which IRAK-inh sensitizes Paclitaxel for apoptosis induction. Although IRAK1-inh plus Paclitaxel led to reduced secretion of IL-6, IL-8 and CXCL1 in Paclitaxel-resistant cells (FIG. 12E), treatments with two IKKβ/NF-κB inhibitors PS1145 and Bay 117082 failed to sensitize Paclitaxel for apoptosis (FIG. 6G). This suggests that in addition to NF-κB pathway, there are additional mechanisms of Paclitaxel resistance linked to IRAK1-engaged modulation of apoptosis induction.

p38/JNK MAPKs are other downstream effectors of IRAK1 signaling that have been implicated in apoptosis modulation[33-35]. Unlike IKKβ/NF-κB inhibitors, we found that the p38 inhibitor was able to phenocopy IRAK-inh to sensitize Paclitaxel-induced apoptosis in Paclitaxel-resistant cells, though this effect was not evident for the JNK inhibitor (FIG. 6G). In line with these findings, both the IRAK-inh and p38 inhibitor, but not the two IKKβ/NF-κB inhibitors (PS1145 and Bay117082), were able to cooperate with Paclitaxel to decrease p-p38 and MCl-1 expression and, which was companied by increased PARP cleavage indicative of apoptosis (FIG. 6H). MCL-1 is known to be phosphorylated and stabilized by p38/JNK to promote survival[36]. In addition, MCL-1 has been recently shown to be crucial for the viability of TNBC cells[37]. Thus, these findings along with the previous reports suggest that one mechanism by which IRAK1-inh sensitizes Paclitaxel for apoptosis induction is by acting to inhibit p38, which in turn decreases MCL-1, though we do not completely exclude the involvement of NF-κB pathway in this scenario.

Together, these findings suggest that both NF-κB and p38-MCL-1 signaling downstream of IRAK1 can be attributed to the progressive development of chemoresistance. While the former is perhaps mainly involved in CSC repopulation and self-renewal, the latter is relevant to promoting a survival mechanism to evade chemotherapy-elicited apoptosis. In light of these observations, we reasoned that therapeutic targeting of IRAK1 may therefore be a more effective strategy to eliminate both, as compared to inhibiting NF-κB alone, advocating a prime target for advanced TNBC (FIG. 6I).

Interestingly, traditional oriental medicine *Ginseng* products Ginsenoside Rb1 and its metabolite compound K (CK) have been recently reported to have the ability to inhibit IRAK1 and thus reduce inflammation response both in vitro and in vivo[38]. We thus evaluated the two Ginsenosides for their capacity to inhibit TNBC aggressive growth and Paclitaxel resistance. The results show that the CK compound, but not the Rb1, was able to mimic the IRAK-inh to inhibit p-IRAK1 in MDA231-LM2 cells (FIG. 13), abolish MDA231-LM2 mammosphere growth (FIG. 13B), and combat Paclitaxel resistance (FIGS. 13C and 13D). Thus, for a translation point of view, this indicate a potential application of *Ginseng* products to tackle metastasis and chemoresistance in advanced TNBC patients with high levels of IRAK1, which might be worthy of further clinical exploration.

DISCUSSION

There are limited treatment options for advanced breast cancers experiencing relapse with distant metastasis. In the present study we unraveled a previously uncharacterized regulatory mechanism operating in TNBC that drives aggressive growth, metastasis and chemoresistance. A major finding of this study is the identification of IRAK1 as an actionable kinase target whose inactivation may provide a valid therapeutic approach to address the current unmet clinical need.

IRAK1 is an active kinase of IL-1/TLR signaling pathway mainly involved in inflammation response. Although IL1-signaling and TLR-MyD88 has been implicated in human cancers, IRAK1 alteration itself has not been previously linked to human malignancy until very recently[20,22,23]. We found that IRAK1 is overexpressed in a subset of breast cancers, mainly in TNBC, and its expression is further associated with metastasis and poor survival. Consistent with a functional role of IRAK1 in TNBC, only TNBC cells that express higher levels of IRAK1 exhibited considerable susceptibility to IRAK1 depletion or pharmacologic inhibition, revealing that IRAK1 can also be exploited as a predictive marker for IRAK1-targeted therapy in the future.

The ability of IRAK1 to affect TNBC progression appears to involve the regulation of NF-κB signaling as evidenced by reduced NF-κB reporter activity and NF-κB target expression upon IRAK1 inhibition. It is known that NF-κB activation in CSC maintains stemness[39,40] Moreover, NF-κB-related cytokines, such as IL-6, IL-8 and CXCL1, have a major role in TNBC tumorigenesis, including growth, metastasis, chemoresistance, as well as cancer stem cell phenotypes[11,12,24]. We detected much increased IRAK1 expression in metastatic clinical tumor samples compared to matched primary tumors. Intriguingly, this was recapitulated in vitro in MDA231 which expresses a low level of IRAK1 but showed increased expression and activity of IRAK1 when they become metastatic, and thus became much more sensitive to IRAK1 inhibition. These findings suggest that metastatic TNBC have a gain of IRAK1-dependency, thus highlighting the potential utility of therapeutic targeting of IRAK1 for metastatic disease. Indeed, we show that IRAK1-inn effectively blocked the metastatic progression in vivo and extended the survival of the mice carrying TNBC metastasis. Although this study focused on the role of IRAK1-driven cytokine network in a cancer cell autonomous manner, IL-1-mediated IRAK1 activation via tumor infiltrating immune cells-tumor cell interaction may further enhance oncogenic activity of IRAK1 in vivo. We therefore expect that therapeutic targeting of IRAK1 may be particularly effective in vivo through abrogating both cancer intrinsic and cancer-promoting immune response, though addressing this aspect will be technically challenging in immune-deficient mice.

Direct targeting NF-κB signaling with therapeutic interventions such as IKKβ/RelA inhibitors has proved a challenge due to severe toxicity in patients[18], thus inhibiting IRAK1 as an alternative approach to target NF-κB in TNBC bears considerable implications for therapeutic treatment. Of important notice, IRAK1 knockout mice shows normal phenotype, which is in contrast to mice lacking RelA or other subunits of IKK complex that are embryonic lethal due to hepatic apoptosis[18,41]. Given the important role of NF-κB and its dependency on IRAK1 in TNBC progression, we reasoned that therapeutic targeting of IRAK1 might be able to achieve cancer selectivity, thus being a more accessible and less deleterious target than NF-κB itself for curtailing TNBC or other high IRAK1 and NF-κB-driven cancers.

We also ascertained the requirement of the kinase activity of IRAK1 in TNBC. It has been shown that depending on cell types and contexts, IRAK1/4 can potentiate inflammatory signals through a scaffold function rather than through kinase activity[28]. For example, although IRAK1/4 kinase activity is essential for human plasmacytoid dendritic cell (pDC) activation, it is dispensable in normal human B, T, dendritic, and monocytic cells[28]. Here we confirm that IRAK1 kinase activity is required for the aggressiveness of TNBC cells as a kinase inactive mutant of IRAK1 was clearly inhibitory for invasive growth and mammosphere formation of TNBC cells. This has notable therapeutic implications as targeted inhibition of IRAK1 kinase activity may allow specific abrogation of IRAK1 kinase activity in cancer cells, without affecting the scaffolding role of IRAK1 in normal immune response.

Another major finding of this study is the identification of IRAK1 activation as a key driver event in acquired resistance to chemotherapy. Increasing evidence has begun to elucidate the crucial roles of chemotherapy-induced inflammatory cytokine or chemokine expression in CSC repopulation and possible tumor recurrence[12,22,30,31,42]. In TNBC, chemotherapy including Paclitaxel has been previously shown to induce cytokine secretion such as IL-6 and IL-8 through activation of various pathways including STAT3, TGFβ and HIF1[32,42,43]. Here we show that IRAK1 signaling is also activated by chemotherapeutic agents, including those widely used Paclitaxel, Doxorubicin and vincristine, which contribute to chemotherapy-induced cytokine expression. Accordingly, chemotherapy-induced mammosphere enrichment is largely attenuated upon IRAK1 inhibition. In line with these findings, we show that TNBC cells with acquired resistance to Paclitaxel exhibited enhanced activity of IRAK1 and inhibition of IRAK1 is able to combat Paclitaxel resistance by inducing massive apoptosis.

Of important note, the efficacy of IRAK1 inhibitor to enhance Paclitaxel-induced apoptosis in our model is related to its ability to inhibit p38 MAPK activity, instead of NF-κB. Indeed, a p38 inhibitor similarly enabled Paclitaxel to induce apoptosis in Paclitaxel resistant cells and both IRAK1 inhibitor and p38 inhibitor induced the downregulation of anti-apoptotic protein MCL-1. By contrast, inhibitors of IKKβ/NF-κB were insufficient to induce similar apoptotic response when combined with Paclitaxel. This finding seems to be consistent with a recent report showing a crucial role for p38 in supporting the metastatic growth of TNBC cells[44]. In addition, depending on cellular context, MCL-1 can be phosphorylated and stabilized by p38 to promote anti-apoptotic effect[36] and has been recently identified as a key survival factor to support the viability of TNBC cells[37]. Thus, we postulate that the gain of IRAK1-p38-MCL-1 dependency upon acquired resistance to Paclitaxel may constitute a key mechanism to withstand chemotherapy-induced apoptosis. Clearly, both NF-κB-related cytokine induction and p38 signaling are involved in Paclitaxel resistance. However, there are major functional differences in their contributions to the acquired resistance process. While the former is believed to be mainly involved in CSC expansion, the latter is more required to maintain the survival capacity.

From a translational point of view, therapeutic targeting of IRAK1 might be an effective therapeutic option for refractory TNBC as it is sufficient to block both NF-κB and p38 signaling. Given that cytotoxic chemotherapy remains standard of care for TNBC, our findings provide the rational for developing more potent and drug-like small molecule inhibitors of IRAK1 kinase for targeting metastatic and recurrent TNBC tumors to improve the efficacy of chemotherapy. In light of this view, our finding that the nature product Ginsenoside compound (CK) is able to phenocopy the IRAK-inh to inhibit TNBC metastatic growth and combat chemoresistance is intriguing as it can be readily tested in clinical trials for chemo-refractory TNBC that express high levels of IRAK1.

In summary, the present invention represents a systematic approach to evaluate p-IRAK1 as a clinically relevant biomarker that will improve the treatment and outcomes of TNBC. Apart from validating the prognostic power of p-IRAK1 (in predicting recurrence risk), study findings will increase the treatment options of TNBC. Potentially, p-IRAK1 can identify paclitaxel-resistant TNBC for further treatment with cisplatin or gemcitabine to reduce the high risk of recurrence. This invention re-defines the benefit of cisplatin and gemcitabine and can allow them to be used more effectively. Further validation in large prospective studies will be needed, but since both cisplatin and gemcitabine are already in use for breast cancer, clinical translation can be expected in the relative near future. This invention also provides data regarding the potential of IRAK1 as a novel therapeutic target.

Whilst there has been described in the foregoing description preferred embodiments of the present invention, it will be understood by those skilled in the technology concerned that many variations or modifications in details of design or construction may be made without departing from the present invention.

REFERENCES

1. Rakha, E. A. & Ellis, I. O. Triple-negative/basal-like breast cancer: review. *Pathology* 41, 40-47 (2009).
2. Cleator, S., Heller, W. & Coombes, R. C. Triple-negative breast cancer: therapeutic options. *Lancet Oncol* 8, 235-244 (2007).
3. Dawood, S. Triple-negative breast cancer: epidemiology and management options. *Drugs* 70, 2247-2258 (2010).
4. Foulkes, W. D., Smith, I. E. & Reis-Filho, J. S. Triple-negative breast cancer. *N Engl J Med* 363, 1938-1948 (2010).
5. Clevers, H. At the crossroads of inflammation and cancer. *Cell* 118, 671-674 (2004).

6. Rakoff-Nahoum, S. & Medzhitov, R. Toll-like receptors and cancer. *Nat Rev Cancer* 9, 57-63 (2009).
7. Coussens, L. M. & Werb, Z. Inflammation and cancer. *Nature* 420, 860-867 (2002).
8. Basseres, D. S. & Baldwin, A. S. Nuclear factor-kappaB and inhibitor of kappaB kinase pathways in oncogenic initiation and progression. *Oncogene* 25, 6817-6830 (2006).
9. Jost, P. J. & Ruland, J. Aberrant NF-kappaB signaling in lymphoma: mechanisms, consequences, and therapeutic implications. *Blood* 109, 2700-2707 (2007).
10. Perkins, N. D. The diverse and complex roles of NF-kappaB subunits in cancer. *Nat Rev Cancer* 12, 121-132 (2012).
11. Hartman, Z. C., et al. Growth of triple-negative breast cancer cells relies upon coordinate autocrine expression of the proinflammatory cytokines IL-6 and IL-8. *Cancer Res* 73, 3470-3480 (2013).
12. Acharyya, S., et al. A CXCL1 paracrine network links cancer chemoresistance and metastasis. *Cell* 150, 165-178 (2012).
13. Yamamoto, M., et al. NF-kappaB non-cell-autonomously regulates cancer stem cell populations in the basal-like breast cancer subtype. *Nat Commun* 4, 2299 (2013).
14. Ginestier, C., et al. CXCR1 blockade selectively targets human breast cancer stem cells in vitro and in xenografts. *J Clin Invest* 120, 485-497 (2010).
15. Baud, V. & Karin, M. Is NF-kappaB a good target for cancer therapy? Hopes and pitfalls. *Nat Rev Drug Discov* 8, 33-40 (2009).
16. Dutta, J., Fan, Y., Gupta, N., Fan, G. & Gelinas, C. Current insights into the regulation of programmed cell death by NF-kappaB. *Oncogene* 25, 6800-6816 (2006).
17. Luo, J. L., Kamata, H. & Karin, M. IKK/NF-kappaB signaling: balancing life and death—a new approach to cancer therapy. *J Clin Invest* 115, 2625-2632 (2005).
18. DiDonato, J. A., Mercurio, F. & Karin, M. NF-kappaB and the link between inflammation and cancer. *Immunol Rev* 246, 379-400 (2012).
19. Tornatore, L., et al. Cancer-Selective Targeting of the NF-kappaB Survival Pathway with GADD45beta/MKK7 Inhibitors. *Cancer Cell* 26, 495-508 (2014).
20. Rhyasen, G. W., et al. Targeting IRAK1 as a therapeutic approach for myelodysplastic syndrome. *Cancer Cell* 24, 90-104 (2013).
21. Srivastava, R., et al. Augmentation of therapeutic responses in melanoma by inhibition of IRAK-1,-4. *Cancer Res* 72, 6209-6216 (2012).
22. Li, Z., et al. Inhibition of IRAK1/4 sensitizes T cell acute lymphoblastic leukemia to chemotherapies. *J Clin Invest* (2015).
23. Scheeren, F. A., et al. A cell-intrinsic role for TLR2-MYD88 in intestinal and breast epithelia and oncogenesis. *Nat Cell Biol* 16, 1238-1248 (2014).
24. Korkaya, H., Liu, S. & Wicha, M. S. Regulation of cancer stem cells by cytokine networks: attacking cancer's inflammatory roots. *Clin Cancer Res* 17, 6125-6129 (2011).
25. Lu, H., et al. A breast cancer stem cell niche supported by juxtacrine signalling from monocytes and macrophages. *Nat Cell Biol* 16, 1105-1117 (2014).
26. Barbie, T. U., et al. Targeting an IKBKE cytokine network impairs triple-negative breast cancer growth. *J Clin Invest* 124, 5411-5423 (2014).
27. Minn, A. J., et al. Genes that mediate breast cancer metastasis to lung. *Nature* 436, 518-524 (2005).
28. Chiang, E. Y., Yu, X. & Grogan, J. L. Immune complex-mediated cell activation from systemic lupus erythematosus and rheumatoid arthritis patients elaborate different requirements for IRAK1/4 kinase activity across human cell types. *J Immunol* 186, 1279-1288 (2011).
29. Rajan, P. & Srinivasan, R. Targeting cancer stem cells in cancer prevention and therapy. *Stem Cell Rev* 4, 211-216 (2008).
30. Sistigu, A., et al. Cancer cell-autonomous contribution of type I interferon signaling to the efficacy of chemotherapy. *Nat Med* 20, 1301-1309 (2014).
31. Kurtova, A. V., et al. Blocking PGE2-induced tumour repopulation abrogates bladder cancer chemoresistance. *Nature* 517, 209-213 (2015).
32. Samanta, D., Gilkes, D. M., Chaturvedi, P., Xiang, L. & Semenza, G. L. Hypoxia-inducible factors are required for chemotherapy resistance of breast cancer stem cells. *Proc Natl Acad Sci USA* 111, E5429-5438 (2014).
33. Wada, T. & Penninger, J. M. Mitogen-activated protein kinases in apoptosis regulation. *Oncogene* 23, 2838-2849 (2004).
34. Cai, B., Chang, S. H., Becker, E. B., Bonni, A. & Xia, Z. p38 MAP kinase mediates apoptosis through phosphorylation of BimEL at Ser-65. *J Biol Chem* 281, 25215-25222 (2006).
35. Chuang, S. M., Wang, I. C. & Yang, J. L. Roles of JNK, p38 and ERK mitogen-activated protein kinases in the growth inhibition and apoptosis induced by cadmium. *Carcinogenesis* 21, 1423-1432 (2000).
36. Thomas, L. W., Lam, C. & Edwards, S. W. Mcl-1; the molecular regulation of protein function. *FEBS Lett* 584, 2981-2989 (2010).
37. Petrocca, F., et al. A genome-wide siRNA screen identifies proteasome addiction as a vulnerability of basal-like triple-negative breast cancer cells. *Cancer Cell* 24, 182-196 (2013).
38. Joh, E. H., Lee, I. A., Jung, I. H. & Kim, D. H. Ginsenoside Rb1 and its metabolite compound K inhibit IRAK-1 activation—the key step of inflammation. *Biochem Pharmacol* 82, 278-286 (2011).
39. Liu, M., et al. The canonical NF-kappaB pathway governs mammary tumorigenesis in transgenic mice and tumor stem cell expansion. *Cancer Res* 70, 10464-10473 (2010).
40. Murohashi, M., et al. Gene set enrichment analysis provides insight into novel signalling pathways in breast cancer stem cells. *Br J Cancer* 102, 206-212 (2010).
41. Huang, Y., Li, T., Sane, D. C. & Li, L. IRAK1 serves as a novel regulator essential for lipopolysaccharide-induced interleukin-10 gene expression. *J Biol Chem* 279, 51697-51703 (2004).
42. Marotta, L. L., et al. The JAK2/STAT3 signaling pathway is required for growth of CD44(+)CD24(-) stem cell-like breast cancer cells in human tumors. *J Clin Invest* 121, 2723-2735 (2011).
43. Bhola, N. E., et al. TGF-beta inhibition enhances chemotherapy action against triple-negative breast cancer. *J Clin Invest* 123, 1348-1358 (2013).
44. Wu, X., et al. Ubiquitin-conjugating enzyme Ubc13 controls breast cancer metastasis through a TAK1-p38 MAP kinase cascade. *Proc Natl Acad Sci USA* 111, 13870-13875 (2014).

The invention claimed is:

1. A therapeutic method for a patient with triple negative breast cancer and resistant to paclitaxel therapy, the method comprising:
   (a) determining the patient has an elevated level of interleukin 1 receptor associated kinase 1 (IRAK1) protein relative to normal levels in healthy individuals by measuring the level of IRAK1 protein in a sample obtained from the patient; and
   (b) treating the patient by administering an inhibitor of IRAK1 activity when the measured level of IRAK1 is elevated relative to normal levels in healthy individuals; wherein the inhibitor of IRAK1 activity is a ginsenoside.

2. A method for treating a patient with triple negative breast cancer and resistant to paclitaxel therapy who has an elevated level of interleukin 1 receptor associated kinase 1 (IRAK1) protein relative to normal levels in healthy individuals as determined by measuring the level of IRAK1 protein in a sample obtained from the patient, the method comprising administering an inhibitor of IRAK1 activity to the patient, wherein the inhibitor of IRAK1 activity is a ginsenoside.

* * * * *

SEQUENCE LISTING

<160> NUMBER OF SEQ ID NOS: 22

<210> SEQ ID NO 1
<211> LENGTH: 19
<212> TYPE: DNA
<213> ORGANISM: artificial sequence
<220> FEATURE:
<223> OTHER INFORMATION: pGIPZ vector; Constitutive KD; IRAK1's ORF

<400> SEQUENCE: 1
aattcatcac tttcttcgg                                                        19

<210> SEQ ID NO 2
<211> LENGTH: 19
<212> TYPE: DNA
<213> ORGANISM: artificial sequence
<220> FEATURE:
<223> OTHER INFORMATION: pGIPZ vector; Constitutive KD; IRAK1's ORF

<400> SEQUENCE: 2
ccatcacttt gtagaagcg                                                        19

<210> SEQ ID NO 3
<211> LENGTH: 19
<212> TYPE: DNA
<213> ORGANISM: artificial sequence
<220> FEATURE:
<223> OTHER INFORMATION: pGIPZ vector; Constitutive KD; IRAK1's UTR

<400> SEQUENCE: 3
acatgaaacc tgacttgct                                                        19

<210> SEQ ID NO 4
<211> LENGTH: 19
<212> TYPE: DNA
<213> ORGANISM: artificial sequence
<220> FEATURE:
<223> OTHER INFORMATION: pTRIPZ vector; Inducible KD; IRAK1's UTR

<400> SEQUENCE: 4
attactcaag gacaacctg                                                        19

<210> SEQ ID NO 5
<211> LENGTH: 22
<212> TYPE: DNA
<213> ORGANISM: artificial sequence
<220> FEATURE:
<223> OTHER INFORMATION: 18S gene; Forward primer

<400> SEQUENCE: 5
cgaacgtctg ccctatcaac tt                                                    22

<210> SEQ ID NO 6
<211> LENGTH: 19
<212> TYPE: DNA
<213> ORGANISM: artificial sequence
<220> FEATURE:
<223> OTHER INFORMATION: 18S gene; reverse primer

<400> SEQUENCE: 6
acccgtggtc accatggta                                                        19

<210> SEQ ID NO 7
<211> LENGTH: 20
<212> TYPE: DNA
<213> ORGANISM: artificial sequence

```
<220> FEATURE:
<223> OTHER INFORMATION: IRAK1 gene; forward primer

<400> SEQUENCE: 7
tcagctttgg ggtggtagtg                                               20

<210> SEQ ID NO 8
<211> LENGTH: 20
<212> TYPE: DNA
<213> ORGANISM: artificial sequence
<220> FEATURE:
<223> OTHER INFORMATION: IRAK1 gene; reverse primer

<400> SEQUENCE: 8
tagatctgca tggcgatggg                                               20

<210> SEQ ID NO 9
<211> LENGTH: 20
<212> TYPE: DNA
<213> ORGANISM: artificial sequence
<220> FEATURE:
<223> OTHER INFORMATION: IRAK2 gene; forward primer

<400> SEQUENCE: 9
tctcaccccc aaacttgctc                                               20

<210> SEQ ID NO 10
<211> LENGTH: 20
<212> TYPE: DNA
<213> ORGANISM: artificial sequence
<220> FEATURE:
<223> OTHER INFORMATION: IRAK2 gene; reverse primer

<400> SEQUENCE: 10
cctcggccaa cactattcca                                               20

<210> SEQ ID NO 11
<211> LENGTH: 20
<212> TYPE: DNA
<213> ORGANISM: artificial sequence
<220> FEATURE:
<223> OTHER INFORMATION: IRAK3 gene; forward primer

<400> SEQUENCE: 11
gcctggcaga gagactttca                                               20

<210> SEQ ID NO 12
<211> LENGTH: 22
<212> TYPE: DNA
<213> ORGANISM: artificial sequence
<220> FEATURE:
<223> OTHER INFORMATION: IRAK3 gene; reverse primer

<400> SEQUENCE: 12
aggactcaac actgctccat ag                                            22

<210> SEQ ID NO 13
<211> LENGTH: 20
<212> TYPE: DNA
<213> ORGANISM: artificial sequence
<220> FEATURE:
<223> OTHER INFORMATION: IRAK4 gene; forward primer

<400> SEQUENCE: 13
agcttgcagc aatggttgac                                               20
```

```
<210> SEQ ID NO 14
<211> LENGTH: 20
<212> TYPE: DNA
<213> ORGANISM: artificial sequence
<220> FEATURE:
<223> OTHER INFORMATION: IRAK 4 gene; reverse primer

<400> SEQUENCE: 14
tgtgccaaga aagtggtgga                                              20

<210> SEQ ID NO 15
<211> LENGTH: 23
<212> TYPE: DNA
<213> ORGANISM: artificial sequence
<220> FEATURE:
<223> OTHER INFORMATION: IL-1beta gene; forward primer

<400> SEQUENCE: 15
gccaatcttc attgctcaag tgt                                          23

<210> SEQ ID NO 16
<211> LENGTH: 20
<212> TYPE: DNA
<213> ORGANISM: artificial sequence
<220> FEATURE:
<223> OTHER INFORMATION: IL-1beta gene; reverse primer

<400> SEQUENCE: 16
ggtcggagat tcgtagctgg                                              20

<210> SEQ ID NO 17
<211> LENGTH: 23
<212> TYPE: DNA
<213> ORGANISM: artificial sequence
<220> FEATURE:
<223> OTHER INFORMATION: IL-6 gene; forward primer

<400> SEQUENCE: 17
agttcctgca gaaaaaggca aag                                          23

<210> SEQ ID NO 18
<211> LENGTH: 20
<212> TYPE: DNA
<213> ORGANISM: artificial sequence
<220> FEATURE:
<223> OTHER INFORMATION: IL-6 gene; reverse primer

<400> SEQUENCE: 18
aaagctgcgc agaatgagat                                              20

<210> SEQ ID NO 19
<211> LENGTH: 20
<212> TYPE: DNA
<213> ORGANISM: artificial sequence
<220> FEATURE:
<223> OTHER INFORMATION: IL-8 gene; forward primer

<400> SEQUENCE: 19
accggaagga accatctcac                                              20

<210> SEQ ID NO 20
<211> LENGTH: 21
<212> TYPE: DNA
<213> ORGANISM: artificial sequence
<220> FEATURE:
<223> OTHER INFORMATION: IL-8 gene; reverse primer
```

```
<400> SEQUENCE: 20
ggcaaaactg caccttcaca c                                        21

<210> SEQ ID NO 21
<211> LENGTH: 18
<212> TYPE: DNA
<213> ORGANISM: artificial sequence
<220> FEATURE:
<223> OTHER INFORMATION: CXCL1 gene; forward primer

<400> SEQUENCE: 21
ccagctcttc cgctcctc                                            18

<210> SEQ ID NO 22
<211> LENGTH: 17
<212> TYPE: DNA
<213> ORGANISM: artificial sequence
<220> FEATURE:
<223> OTHER INFORMATION: CXCL1 gene; reverse primer

<400> SEQUENCE: 22
cacggacgct cctgctg                                             17
```